United States Patent
Stankovic et al.

(10) Patent No.: US 12,390,510 B2
(45) Date of Patent: Aug. 19, 2025

(54) METHODS OF TREATING SENSORINEURAL HEARING LOSS USING FIBROBLAST GROWTH FACTOR 2 (FGF2)

(71) Applicant: Massachusetts Eye and Ear Infirmary, Boston, MA (US)

(72) Inventors: Konstantina Stankovic, Boston, MA (US); Nadia A. Atai, Boston, MA (US); Brad Welling, Boston, MA (US); Richard Seist, Cambridge, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 86 days.

(21) Appl. No.: 17/614,845

(22) PCT Filed: May 29, 2020

(86) PCT No.: PCT/US2020/035198
§ 371 (c)(1),
(2) Date: Nov. 29, 2021

(87) PCT Pub. No.: WO2020/243478
PCT Pub. Date: Dec. 3, 2020

(65) Prior Publication Data
US 2022/0226437 A1 Jul. 21, 2022

Related U.S. Application Data

(60) Provisional application No. 62/854,287, filed on May 29, 2019.

(51) Int. Cl.
*A61K 38/18* (2006.01)
*A61K 9/00* (2006.01)
*A61P 27/16* (2006.01)

(52) U.S. Cl.
CPC ........ *A61K 38/1825* (2013.01); *A61K 9/0046* (2013.01); *A61P 27/16* (2018.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 6,927,204 B2 | 8/2005 | Gao | |
| 2010/0273864 A1 | 10/2010 | Lichter et al. | |
| 2011/0319377 A1 | 12/2011 | Lichter et al. | |
| 2017/0029511 A1 | 2/2017 | Saragovi et al. | |
| 2018/0117115 A1 | 5/2018 | Kopke et al. | |

FOREIGN PATENT DOCUMENTS

| | | | |
|---|---|---|---|
| JP | WO2009/157558 | * 12/2009 | |
| WO | WO 2018/007597 | 1/2018 | |
| WO | WO 2018/111926 | 6/2018 | |

OTHER PUBLICATIONS

WO2009157558—machine translation from WIPO site, accessed on Nov. 18, 2023.*
D'Sa et al. Plasticity of synaptic endings in the cochlear nucleus following noise-induced hearing loss is facilitated in the adult FGF2 overexpressor mouse. Eur. J. Neurosci. 26: 666-680, 2007.*
Sergeyenko et al. Age-Related Cochlear Synaptopathy: An Early-Onset Contributor to Auditory Functional Decline, J. Neurosci. 33(34): 13686-13694, 2013.*
Acharya et al., "A pilot study investigating basic fibroblast growth factor for the repair of chronic tympanic membrane perforations in pediatric patients," International journal of pediatric otorhinolaryngology, Mar. 2015, 79(3):332-335.
Akita et al., "Basic fibroblast growth factor accelerates and improves second-degree burn wound healing," Wound Repair and Regeneration, Sep.-Oct. 2008, 16(5):635-641.
Aviles et al., "Testing clinical therapeutic angiogenesis using basic fibroblast growth factor (FGF-2)," Br J Pharmacol., Oct. 2003, 140(4):637-646.
Bang et al., "Farnesyl pyrophosphate is a novel pain-producing molecule via specific activation of TRPV3," J. Biol. Chem., Jun. 2010, 285(25):19362-19371.
Bauer et al., "Primary afferent dendrite degeneration as a cause of tinnitus," J. Neurosci. Res., May 2007, 85(7):1489-1498.
Borden et al., "Hyaluronic acid hydrogel sustains the delivery of dexamethasone across the round window membrane," Audiol Neurootol., 2011, 16(1):1-11.
Briz et al., "Activity-dependent rapid local RhoA synthesis is required for hippocampal synaptic plasticity," J. Neurosci., Feb. 2015, 35(5):2269-2282.
Chan et al., "Detection of necrosis by release of lactate dehydrogenase activity," Methods in molecular biology, 2013, 979:65-70.
Chen et al., "Oral steroid treatment of sudden sensorineural hearing loss: a ten year retrospective analysis," Otol Neurotol, Sep. 2003, 24(5):728-733.
Cheng et al., "Farnesyltransferase haplodeficiency reduces neuropathology and rescues cognitive function in a mouse model of Alzheimer disease," J. Biol. Chem., Dec. 2013, 288(50):35952-35960.
ClinicalTrials.gov [online], "Fibroblast Growth Factor Regeneration of Tympanic Membrane Perforations," Dec. 31, 2020, retrieved on Apr. 25, 2023, retrieved from URL<clinicaltrials.gov/ct2/show/NCT02307916?term=welling&rank=1>, 8 pages.
ClinicalTrials.gov [online], "Safety, Tolerability and Efficacy for CGF166 in Patients With Unilateral or Bilateral Severe-to-profound Hearing Loss," Oct. 8, 2021, retrieved on Apr. 27, 2023, retrieved from URL<https://clinicaltrials.gov/ct2/show/study/NCT02132130>, 10 pages.
Cochran et al., "A Randomized Clinical Trial Evaluating rh-FGF-2/β-TCP in Periodontal Defects," Journal of dental research, May 2016, 95(5):523-530.

(Continued)

*Primary Examiner* — Christine J Saoud
(74) *Attorney, Agent, or Firm* — Fish & Richardson P.C.

(57) ABSTRACT

Methods of using Fibroblast growth factor 2 (FGF2) to treat subjects with hearing loss associated with impaired word recognition.

9 Claims, 7 Drawing Sheets
(5 of 7 Drawing Sheet(s) Filed in Color)
Specification includes a Sequence Listing.

(56) References Cited

OTHER PUBLICATIONS

Crane et al., "Steroids for treatment of sudden sensorineural hearing loss: a meta-analysis of randomized controlled trials," Laryngoscope, Jan. 2015, 125(1):209-217.
Crowson et al., "Emerging Therapies for Sensorineural Hearing Loss," Otology & Neurotology, Apr. 2017, 38(6):792-803.
Davila et al., "Sensory impairment among older US workers," Am J Public Health, Aug. 2009, 99(8):1378-1385.
de Santana et al., "Human intrabony defect regeneration with rhFGF-2 and hyaluronic acid—a randomized controlled clinical trial," Journal of Clinical Periodontology, Jul. 2015, 42(7):658-665.
Dilwali et al., "Secreted Factors from Human Vestibular Schwannomas Can Cause Cochlear Damage," Scientific Reports, Dec. 2015, 5:18599, 13 pages.
Dvorak et al., "Repair of Chronic Tympanic Membrane perforations with Long-Term Epidermal Growth Factor," Laryngoscope, Dec. 1995, 105(12):1300-1304.
Ebeid and Huh, "FGF signaling: diverse roles during cochlear development," BMB Rep, Oct. 2017, 50(10): 487-495.
Ebert et al., "Induced pluripotent stem cells from a spinal muscular atrophy patient," Nature, Dec. 2008, 457:277-280.
El Kechai et al., "Recent advances in local drug delivery to the inner ear," Int J Pharm., Oct. 2015, 494(1):83-101.
Escobar-Chávez et al., "Applications of thermo-reversible pluronic F-127 gels in pharmaceutical formulations," J Pharm Pharm Sci., 2006, 9(3):339-358.
Fariñas et al., "Spatial shaping of cochlear innervation by temporally regulated neurotrophin expression," The Journal of Neuroscience, Aug. 2001, 21(16):6170-6180.
Fina et al., "Direct Application of Basic Fibroblast Growth Factor Improved Tympanic Membrane perforation Healing," Laryngoscope, Jul. 1993, 103(7):804-809.
Fina et al., "Improved Healing of Tympanic Membrane Perforations with Basic Fibroblast Growth Factor," Growth Factors, 1991, 5(4):265-272.
Fu et al., "Randomised placebo-controlled trial of use of topical recombinant bovine basic fibroblast growth factor for second-degree burns," Lancet, Nov. 1998, 352(9141):1661-1664.
Furman et al., "Noise-induced cochlear neuropathy is selective for fibers with low spontaneous rates," J Neurophysiol, Aug. 2013, 110(3):577-586.
Ge et al., "Distribution of PLGA nanoparticles in chinchilla cochleae," Otolaryngol Head Neck Surg., Oct. 2007, 137(4):619-23.
Giusti and Bianchi, "Treatment of complex regional pain syndrome type I with bisphosphonates," RMD Open, 2015, 1(Suppl 1):1-6.
Glueckert et al., "Anatomical basis of drug delivery to the inner ear," Hear Res., Oct. 2018, 368:10-27.
Grothe et al., "Physiological function and putative therapeutic impact of the FGF-2 system in peripheral nerve regeneration—lessons from in vivo studies in mice and rats," Brain Res Rev, Aug. 2006, 51(2):293-299.
Hachem et al., "Glutamate Increases in Vitro Survival and Proliferation and Attenuates Oxidative Stress-Induced Cell Death in Adult Spinal Cord-Derived Neural Stem/Progenitor Cells via Non-NMDA Ionotropic Glutamate Receptor," Stem Cells Dev, Aug. 2016, 25(16):1223-1233.
Haditsch et al., "A central role for the small GTPase Rac1 in hippocampal plasticity and spatial learning and memory," Mol. Cell. Neurosci., Jul. 2009, 41(4):409-419.
Hakuba et al., "A new method for closing tympanic membrane perforations using basic fibroblast growth factor," The Laryngoscope, Aug. 2003, 113(8):1352-1355.
Hakuba et al., "Basic fibroblast growth factor combined with atelocollagen for closing chronic tympanic membrane perforations in 87 patients," Otology & Neurotology, Jan. 2010, 31(1):118-121.
Hakuba et al., "Gelatin hydrogel with basic fibroblast growth factor for tympanic membrane regeneration," Otol Nuerotol., Mar. 2014, 35(3):540-44.
Halpin et al., "Audiology in the sudden hearing loss clinical trial," Otol Neurotol, Aug. 2012, 33(6):907-911.
Han and Liu, "Autologous free fat particle grafting combined with bFGF to repair facial depression," Zhongguo xiu fu chongjian wai ke za zhi, Chinese journal of reparative and reconstructive surgery, Mar. 2008, 22(3):339-342, 6 pages (with English abstract).
Hansen et al., "Reciprocal signaling between spiral ganglion neurons and Schwann cells involves neuregulin and neurotrophins," Hear. Res., Nov. 2001, 161(1-2):87-98.
Havenith et al., "Spiral ganglion cell survival after round window membrane application of brain-derived neurotrophic factor using gelfoam as carrier," Hearing Research, Feb. 2011, 272(1-2):168-177.
Hirano et al., "Regeneration of aged vocal fold: first human case treated with fibroblast growth factor," The Laryngoscope, Dec. 2008, 118(12):2254-2259.
Horie et al., "Sustained delivery of lidocaine into the cochlea using poly lactic/glycolic acid microparticles," Laryngoscope, Feb. 2010, 120(2):377-83.
Hottman and Li, "Protein prenylation and synaptic plasticity: implications for Alzheimer's disease," Mol Neurobiol., Aug. 2014, 50(1):177-185.
Huang et al., "Chronic diseases and risk for depression in old age: a meta-analysis of published literature," Ageing Research Reviews, Apr. 2010, 9(2):131-141.
Huang et al., "The effect of recombinant bovine basic fibroblast growth factor on the LASIK-induced neurotrophic epitheliopathy and the recovery of corneal sensation after LASIK," Zhonghuayan ke zazhi, Chinese Journal of Ophthalmology, Jan. 2011, 47(1):22-26, 2 pages (English Abstract Only).
Hull et al., "Healing with basic fibroblast growth factor is associated with reduced indomethacin induced relapse in a human model of gastric ulceration," Gut, Feb. 1997, 40(2):204-210.
Hyun et al., "In vitro and in vivo release of albumin using a biodegradable MPEG-PCL diblock copolymer as an in situ gel-forming carrier," Biomacromolecules, Apr. 2007, 8(4):1093-100.
Igai et al., "Tracheal cartilage regeneration by slow release of basic fibroblast growth factor from a gelatin sponge," J Thorne Cardiovasc Surg., Jul. 2007, 134(1):170-5.
Inaoka et al., "Local application of hepatocyte growth factor using gelatin hydrogels attenuates noise-induced hearing loss in guinea pigs," Acta Otolaryngol., Apr. 2009, 129(4):453-7.
International Preliminary Report on Patentability in International Appln. No. PCT/US2020/035198, mailed on Dec. 9, 2021, 10 pages.
International Search Report and Written Opinion in International Appln. No. PCT/US2020/035198, mailed on Sep. 4, 2020, 13 pages.
Jan et al., "Third-generation bisphosphonates for cochlear otosclerosis stabilizes sensorineural hearing loss in long-term follow-up," Laryngosc. Invest. Otolaryngol., Sep. 2017, 2(5):262-268.
Jensen et al., "Immediate and delayed cochlear neuropathy after noise exposure in pubescent mice," PLoS One, May 2015, 10(5):e125160, 17 pages.
Jia et al., "Prolonged alendronate treatment prevents the decline in serum TGF-β1 levels and reduces cortical bone strength in long-term estrogen deficiency rat model," Bone, 2013, 52(2013):424-432.
Jin et al., "Expression and localization of K channels KCNQ2 and KCNQ3 in the mammalian cochlea," Audiology & Neuro-otology, Oct. 2008, 14(2):98-105.
Kakigi et al., "The effects of basic fibroblast growth factor on postoperative mastoid cavity problems," Otology & Neurotology, May 2005, 26(3):333-336.
Kanemaru et al., "Regenerative treatment for tympanic membrane perforation," Otology & Neurotology, Oct. 2011, 32(8):1218-1223.
Kao et al., "Activation of TRAIL-DR5 pathway promotes sensorineural degeneration in the inner ear," Aging Cell, Apr. 2016, 15(2):301-308.
Kao et al., "Loss of osteoprotegerin expression in the inner ear causes degeneration of the cochlear nerve and sensorineural hearing loss," Neurobiol Dis, Aug. 2013, 56:25-33.
Kase et al., "Poster: Influence of topical application of basic fibroblast growth factor upon inner ear," Poster, Presented at Pro-

(56) References Cited

OTHER PUBLICATIONS ceedings of the 2007 Annual Meeting of the American Academy of Otolaryngology—Head and Neck Surgery, Washington D.C., Sep. 16-19, 2007, 1 page.
Kato and Jackler, "Repair of Chronic Tympanic Membrane Perforations with Fibroblast Growth Factor," Otolaryngol Head Neck Surg., Dec. 1996, 115(6):538-547.
Kavanagh et al., "The molecular mechanism of nitrogen-containing bisphosphonates as antiosteoporosis drugs," Proc. Natl. Acad. Sci. U.S.A., May 2006, 103(20):7829-7834.
Kawaguchi et al., "Local application of recombinant human fibroblast growth factor-2 on bone repair: a dose-escalation prospective trial on patients with osteotomy," Journal of Orthopaedic Research, Apr. 2007, 25(4):480-487.
Keithley et al., "GDNF protects the cochlea against noise damage," NeuroReport, Jul. 1998, 9(10):2183-2187.
Kempfle et al., "Bisphosphonate-Linked TrkB Agonist: Cochlea-Targeted Delivery of a Neurotrophic Agent as a Strategy for the Treatment of Hearing Loss," Bioconjug Chem, Apr. 2018, 29(4):1240-1250, 11 pages.
Kendig and Tarloff, "Inactivation of lactate dehydrogenase by several chemicals: implications for in vitro toxicology studies," Toxicology in Vitro, Feb. 2007, 21(1):125-132.
Kennedy et al., "The effects of etidronate disodium on progressive hearing loss from otosclerosis," Otolaryngol. Head Neck Surg., Sep. 1993, 109(3):461-467.
Kitamura et al., "Periodontal tissue regeneration using fibroblast growth factor-2: randomized controlled phase II clinical trial," PLoS One, Jul. 2008, 3(7):e26 11, 11 pages.
Kujawa and Libermann, "Acceleration of age-related hearing loss by early noise exposure: evidence of a misspent youth," J. Neurosci., Feb. 2006, 26(7):2115-2123.
Kujawa and Libermann, "Adding insult to injury: cochlear nerve degeneration after "temporary" noise-induced hearing loss," The Journal of Neuroscience, Nov. 2009, 29(45):14077-14085.
Kuroda et al., "A pilot study of regenerative therapy using controlled release of recombinant human fibroblast growth factor for patients with pre-collapse osteonecrosis of the femoral head," International Orthopaedics, Aug. 2016, 40(8):1747-1754, 9 pages.
Kusuhara et al., "Randomized controlled trial of the application of topical b-FGF-impregnated gelatin microspheres to improve tissue survival in subzone II fingertip amputations," J Hand Surg Eur vol., Jul. 2011, 36(6):455-460.
Landegger et al., "A synthetic AAV vector enables safe and efficient gene transfer to the mammalian inner ear," Nat Biotechnol, Mar. 2017, 35(3):280-284.
Landegger et al., "Neonatal murine cochlear explant technique as an in vitro screening tool in hearing research," J. Vis. Exp., Jun. 2017, 124:e55704, 8 pages.
Lederman et al., "Therapeutic angiogenesis with recombinant fibroblast growth factor-2 for intermittent claudication (the TRAFFIC study): a randomised trial," Lancet, Jun. 2002, 359(9323):2053-2058.
Lee et al., "Ciclopirox protects mitochondria from hydrogen peroxide toxicity," British Journal of Pharmacology, Jun. 2005, 145(4):469-476.
Li et al., "Etidronate rescues cognitive deficits through improving synaptic transmission and suppressing apoptosis in 2-vessel occlusion model rats," J. Neurochem., Feb. 2017, 140(3):476-484.
Li et al., "Geranylgeranyltransferase I mediates BDNF-induced synaptogenesis," J. Neurochem., Jun. 2013, 125(5):698-712.
Li et al., "Protein prenylation constitutes an endogenous brake on axonal growth," Cell Rep., Jul. 2016, 16(2):545-558.
Liberman et al., "Cochlear synaptopathy in acquired sensorineural hearing loss: manifestations and mechanisms," Hear. Res., Jun. 2017, 349:138-147.
Liberman et al., "Toward a differential diagnosis of hidden hearing loss in humans," PLoS One, Sep. 2016, 11:e162726, 15 pages.
Lin et al., "Hearing loss and cognition in the Baltimore Longitudinal Study of Aging," Neuropsychology, Nov. 2011, 25(6):763-770.

Lin et al., "Hearing loss and incident dementia," Archives of Neurology, Feb. 2011, 68(2):214-220.
Liu et al., "Absorbable shanching satin rb-bFGF prepreg sheet and expansion hemostatic sponge together to cure epistaxis with blood disease," Lin Chung Er Bi Yan Hou Tou Jing Wai Ke Za Zhi, Journal of Clinical Otorhinolaryngology, Head, and Neck Surgery, Jan. 2014, 28(2):126-128, 1 page (English Abstract Only).
Liu et al., "Efficacy of bFGF atomization inhalation on postoperative sore throat following oral and maxillofacial surgery under general anesthesia," Shanghai kou qiang yi xue, Shanghai journal of stomatology, Aug. 2016, 25(4):497-499, 1 page (English Abstract Only).
Liu et al., "Otic drug delivery systems: formulation principles and recent developments," Drug Dev Ind Pharm., Sep. 2018, 44(9):1395-1408, 15 pages.
Locher et al., "Neurosensory development and cell fate determination in the human cochlea," Neural Development, Oct. 2013, 8:20, 14 pages.
Loo et al., "From short peptides to nanofibers to macromolecular assemblies in biomedicine," Biotechnology Advances, May-Jun. 2012, 30(3):593-603.
Lou et al., "Analysis of the effectiveness of basic fibroblast growth factor treatment on traumatic perforation of the tympanic membrane at different time points," American journal of otolaryngology, Mar.-Apr. 2012, 33(2):244-249.
Lou et al., "Effects of basic fibroblast growth factor dose on traumatic tympanic membrane perforation," Growth Factors, Oct. 2014, 32(5):150-4.
Low et al., "Basic fibroblast growth factor (FGF-2) protects rat cochlear hair cells in organotypical culture from aminoglycoside injury," J Cell Physiol, Jun. 1996, 167(3):443-450.
Malgrange et al., "Targeting cholesterol homeostasis to fight hearing loss: a new perspective," Front. Aging Neurosci., Jan. 2015, 7:3, 7 pages.
Manzano-Moreno et al., "Bisphosphonate modulation of the gene expression of different markers involved in osteoblast physiology: possible implications in bisphosphonate-related osteonecrosis of the jaw," Int. J. Med. Sci., Feb. 2018, 15(4):359-367.
Marui et al., "A novel approach to therapeutic angiogenesis for patients with critical limb ischemia by sustained release of basic fibroblast growth factor using biodegradable gelatin hydrogel: an initial report of the phase I-IIa study," Circulation Journal, Aug. 2007, 71(8):1181-1186.
McNeish et al., "From Dish to Bedside: Lessons Learned While Translating Findings from a Stem Cell Model of Disease to a Clinical Trial," Cell Stem Cell, Jul. 2015, 17(1):8-10.
Meduri et al., "Effect of the combination of basic fibroblast growth factor and cysteine on corneal epithelial healing after photorefractive keratectomy in patients affected by myopia," Indian journal of ophthalmology, Apr. 2014, 62(4):424-428.
Mercier et al., "Energy extraction from the biologic battery in the inner ear," Nat Biotechnol., Dec. 2012, 30(12):1240-1243, 5 pages.
Mohammadian et al., "Application of stem cell for the regeneration of spiral ganglion neurons," Cell Mol Biol (Noisy-le-grand), Jan. 2017, 63(1):28-33, 7 pages.
Mondain and Ryan, "Effect of Basic Fibroblast Growth Factor on Normal Tympanic Membrane," Am J Otolaryngol., Sep.-Oct. 1994, 15(5):344-350.
Mondain and Ryan, "Epidermal Growth Factor and Basic Fibroblast Growth Factor are Induced in Guinea-pig Tympanic Membrane Following Traumatic Perforation," Acta Otolaryngol (Stockh)., Jan. 1995, 115(1):50-4.
Mondain and Ryan, "Histological Study of the Healing of Traumatic Tympanic Membrane Perforation after Basic Fibroblast Growth Factor Application," Laryngoscope, Mar. 1993, 103(3):312-318.
Mondain et al., "Fibroblast Growth Factor Improved the Healing of Experimental Tympanic Membrane Perforations," Acta Otolaryngol (Stockh), 1991, 111(2):337-341.
Morimoto et al., "Novel collagen/gelatin scaffold with sustained release of basic fibroblast growth factor: clinical trial for chronic skin ulcers," Tissue Engineering Part A, Sep. 2013, 19(17-18):1931-1940.

(56) References Cited

OTHER PUBLICATIONS

Mu et al., "Effects of bFGF on the nasal mucosa after endoscopic sinus surgery," Lin chuang er bi yan hou ke za zhi, Journal of clinical otorhinolaryngology, Jul. 2005, 19(14):646-647, 1 page (English Abstract Only).

Musazzi et al., "Innovative pharmaceutical approaches for the management of inner ear disorders," Drug Deliv Transl Res., Apr. 2018, 8(2):436-449, 24 pages.

Muurling et al., "Metabolomic and network analysis of pharmacotherapies for sensorineural hearing loss," Otology & Neurotology, Jan. 2014, 35(1):1-6.

Nayagam et al., "The spiral ganglion: connecting the peripheral and central auditory systems," Hear. Res., Apr. 2011, 278(1-2):2-20.

Nyberg et al., "Delivery of therapeutics to the inner ear: The challenge of the blood-labyrinth barrier," Sci Transl Med., Mar. 2019, 11(482):eaao0935, 12 pages.

Ohuchi et al., "Established Stem Cell Model of Spinal Muscular Atrophy Is Applicable in the Evaluation of the Efficacy of Thyrotropin-Releasing Hormone Analog," Stem Cells Transl Med, Feb. 2016, 5(2):152-163.

Omae et al., "Regenerative treatment for tympanic membrane perforation using gelatin sponge with basic fibroblast growth factor," Auris Nasus Larynx, Dec. 2017, 44(6):664-671.

Pahnke et al., "Overexpression of glial cell line-derived neurotrophic factor induces genes regulating migration and differentiation of neuronal progenitor cells," Exp. Cell Res., Jul. 2004, 297(2):484-494.

Park et al., "Human farnesyl pyrophosphate synthase is allosterically inhibited by its own product," Nat. Commun., Jan. 2017, 8:14132, 8 pages.

Park et al., "Pravastatin attenuates noise-induced cochlear injury in mice," Neuroscience, Apr. 2012, 208:123-132.

Paşca et al., "Using iPSC-derived neurons to uncover cellular phenotypes associated with Timothy syndrome," Nature Medicine, Nov. 2011, 17(12):1657-1662.

Paulson et al., "A Novel Controlled Local Drug Delivery System for Inner Ear Disease," Laryngoscope, Apr. 2008, 118(4):706-11.

Pazianas and Abrahamsen, "Safety of bisphosphonates," Bone, Jul. 2011, 49(1):103-110.

Piu et al., "OTO-104: a sustained-release dexamethasone hydrogel for the treatment of otic disorders," Otol Neurotol., Jan. 2011, 32(1):171-9.

Pronk et al., "Prospective effects of hearing status on loneliness and depression in older persons: identification of subgroups," International Journal of Audiology, Dec. 2011, 50(12):887-896.

Quesnel et al., "Third-generation bisphosphonates for treatment of sensorineural hearing loss in otosclerosis," Otol. Neurotol., Oct. 2012, 33(8):1308-1314, 14 pages.

Rak et al., "Effects of the neurotrophic factors BDNF, NT-3, and FGF2 on dissociated neurons of the cochlear nucleus," Neuroreport, Jun. 2014, 25(12):960-964.

Reid et al., "Ototoxicity associated with intravenous bisphosphonate administration," Calcif. Tissue Int., Jun. 1995, 56(6):584-585.

Richter et al., "Fluvastatin protects cochleae from damage by high-level noise," Sci. Rep., Feb. 2018, 8:3033, 12 pages.

Rivera et al., "Drug delivery to the inner ear: strategies and their therapeutic implications for sensorineural hearing loss," Curr Drug Deliv., May 2012, 9(3):231-42.

Robson et al., "The safety and effect of topically applied recombinant basic fibroblast growth factor on the healing of chronic pressure sores," Annals of Surgery, Oct. 1992, 216(4):401-406.

Rollin et al., "Natural History of Pediatric Tympanic Membrane Perforation," Otology & Neurotology, Feb. 2011, 32(2):246-251.

Roy et al., "HMG-CoA Reductase Inhibitors Bind to PPARα to Upregulate Neurotrophin Expression in the Brain and Improve Memory in Mice," Cell Metab., Aug. 2015, 22(2):253-265.

Ruel et al., "Neuroprotective effect of riluzole in acute noise-induced hearing loss," Neuroreport, Jul. 2005, 16(10):1087-1090.

Ruel et al., "Physiology, pharmacology and plasticity at the inner hair cell synaptic complex," Hear Res, May 2007, 227(1-2):19-27.

Rüttiger et al., "The reduced cochlear output and the failure to adapt the central auditory response causes tinnitus in noise exposed rats," PLoS One, Mar. 2013, 8(3):e57247, 11 pages.

Sakamoto et al., "Inner ear drug delivery system from the clinical point of view," Acta Otolaryngol Suppl., Nov. 2010, 130(563):101-4.

Salt and Hirose, "Communication pathways to and from the inner ear and their contributions to drug delivery," Hear Res., May 2018, 362:25-37.

Salt and Plontke, "Principles of local drug delivery to the inner ear," Audiol Neurootol., Nov. 2009, 14(6):350-360.

Schaette and McAlpine, "Tinnitus with a normal audiogram: physiological evidence for hidden hearing loss and computational model," J. Neurosci., Sep. 2011, 31(38):13452-13457.

Schuknecht and Woellner, "An experimental and clinical study of deafness from lesions of the cochlear nerve," J Laryngol Otol, Feb. 1955, 69(2):75-97.

Seist et al., "Regeneration of Cochlear Synapses by Systemic Administration of a Bisphosphonate," Front Mol Neurosci., Jul. 2020, 13:87, 11 pages.

Sellke et al., "Therapeutic angiogenesis with basic fibroblast growth factor: technique and early results," The Annals of Thoracic Surgery, Jun. 1998, 65(6):1540-1544.

Senn et al., "NANOCI-Nanotechnology Based Cochlear Implant With Gapless Interface to Auditory Neurons," Otology & Neurotology, Sep. 2017, 38(8):e224-e231.

Shcheglovitov et al., "SHANK3 and IGF1 restore synaptic deficits in neurons from 22q13 deletion syndrome patients," Nature, Nov. 2013, 503(7475):267-271, 7 pages.

Shi et al., "Construction of bicistronic eukaryotic vector containing basic fibroblast growth factor and study of their functions in gene therapy for hearing impairment," Zhonghua er bi yan hou ke za zhi, Feb. 2003, 38(1):21-23, 1 page (English Abstract Only).

Silva et al., "Human iPSC-Derived Neuronal Model of Tau-A152T Frontotemporal Dementia Reveals Tau-Mediated Mechanisms of Neuronal Vulnerability," Stem Cell Reports, Sep. 2016, 7(3):325-340.

Sly et al., "Applying neurotrophins to the round window rescues auditory function and reduces inner hair cell synaptopathy after noise-induced hearing loss," Otol. Neurotol., Oct. 2016, 37(9):1223-1230.

Smith et al., "A simple protocol for using a LDH-based cytotoxicity assay to assess the effects of death and growth inhibition at the same time," PLoS One, 2011, 6(11):e26908, 6 pages.

Su and Huang, "Etidronate protects chronic ocular hypertension induced retinal oxidative stress and promotes retinal ganglion cells growth through IGF-1 signaling pathway," Eur. J. Pharmacol, Dec. 2018, 841:75-81.

Sundberg et al., "Purkinje cells derived from TSC patients display hypoexcitability and synaptic deficits associated, with reduced FMRP levels and reversed by rapamycin," Mol Psychiatry, Nov. 2018, 23(11):2167-2183.

Suzuki et al., "Round-window delivery of neurotrophin 3 regenerates cochlear synapses after acoustic overexposure," Sci. Rep., Apr. 2016, 6:24907, 11 pages.

Takemoto et al., "Preparation of collagen/gelatin sponge scaffold for sustained release of bFGF," Tissue Eng Part A, Oct. 2008, 14(10):1629-38.

Tamura et al., "Drug Delivery to the Cochlea Using PLGA Nanoparticles," Laryngoscope, Nov. 2005, 115(11):2000-5.

Tolias et al., "Control of synapse development and plasticity by Rho GTPase regulatory proteins," Prog. Neurobiol., Jul. 2011, 94(2):133-148.

Vrabec et al., "Evaluation of Basic Fibroblast Growth Factor in Tympanic Membrane Repair," Laryngoscope, Sep. 1994, 104(9):1059-64.

Wainger et al., "Intrinsic membrane hyperexcitability of amyotrophic lateral sclerosis patient-derived motor neurons," Cell Rep, Apr. 2014, 7(1):1-11.

Wang and Green, "Functional role of neurotrophin-3 in synapse regeneration by spiral ganglion neurons on inner hair cells after excitotoxic trauma in vitro," J. Neurosci., May 2011, 31(21):7938-7949.

(56) References Cited

OTHER PUBLICATIONS

Wang et al., "Dose-dependent sustained release of dexamethasone in inner ear cochlear fluids using a novel local delivery approach," Audiol Neurootol., 2009, 14(6):393-401.

Wang et al., "Kainic acid-mediated excitotoxicity as a model for neurodegeneration," Mol Neurobiol, 2005, 31(1-3):3-16.

Wang et al., "Principles of inner ear sustained release following intratympanic administration," Laryngoscope, Feb. 2011, 121(2):385-91.

Wang et al., "Transient receptor potential cation channel subfamily vanilloid 4 and 3 in the inner ear protect hearing in mice," Front. Mol. Neurosci., Dec. 2019, 12:296, 13 pages.

Wei et al., "Survival, synaptogenesis, and regeneration of adult mouse spiral ganglion neurons in vitro," Dev Neurobiol, Jan. 2007, 67(1):108-122.

Weissmiller and Wu, "Current advances in using neurotrophic factors to treat neurodegenerative disorders," Transl. Neurodegen., Jul. 2012, 1:14, 9 pages.

West et al., "Revealing Hearing Loss: A Survey of How People Verbally Disclose Their Hearing Loss," Ear and Hearing, Mar.-Apr. 2016, 37(2):194-205.

WHO.int [online], "Deafness and hearing loss," available on or before Aug. 31, 2018, via Internet Archive: Wayback Machine URL <http://web.archive.org/web/20180831180833/https://www.who.int/news-room/fact-sheets/detail/deafness-and-hearing-loss>, retrieved on Apr. 27, 2023, URL<https://www.who.int/news-room/fact-sheets/detail/deafness-and-hearing-loss>, 7 pages.

Wilson et al., "Global hearing health care: new findings and perspectives," Lancet, Dec. 2017, 390(10111):2503-2515, 13 pages.

Woodbury and Ikezu, "Fibroblast growth factor-2 signaling in neurogenesis and neurodegeneration," J Neuroimmune Pharmacol, Mar. 2014, 9(2):92-101.

Yamahara et al., "Insulin-like growth factor 1 promotes cochlear synapse regeneration after excitotoxic trauma in vitro," Hear. Res., Mar. 2019, 374:5-12.

Yamasoba et al., "Absence of hair cell protection by exogenous FGF-1 and FGF-2 delivered to guinea pig cochlea in vivo," Noise Health, 2001, 3(11):65-78.

Yaşil et al., "Further hearing loss during osteoporosis treatment with etidronate," Postgrad. Med. J., Jun. 1998, 74(872):363-364.

Yin et al., "TGF-β1 increases GDNF production by upregulating the expression of GDNF and furin in human granulosa-lutein cells," Cells, Jan. 2020, 9(1):185, 18 pages.

Ylikoski et al., "Guinea pig auditory neurons are protected by glial cell line-derived growth factor from degeneration after noise trauma," Hear. Res., Oct. 1998, 124(1-2):17-26.

Yonemitsu et al., "DVC1-0101 to treat peripheral arterial disease: a Phase I/IIa open-label dose-escalation clinical trial," Molecular Therapy, Mar. 2013, 21(3):707-714.

Zhai et al., "Basic fibroblast growth factor protects auditory neurons and hair cells from glutamate neurotoxicity and noise exposure," Acta Otolaryngol, Mar. 2004, 124(2):124-129.

Zhai et al., "Protective effect of basic fibroblast growth factor on auditory hair cells after noise exposure," Acta Otolaryngol, Jun. 2002, 122(4):370-373.

Zhang and Lou, "Impact of basic fibroblast growth factor on healing of tympanic membrane perforations due to direct penetrating trauma: a prospective non-blinded/controlled study," Clin Otolaryngol., Dec. 2012, 37(6):445-51.

Zhang et al., "Rapid single-step induction of functional neurons from human pluripotent stem cells," Neuron, Jun. 2013, 78(5):785-798.

Zhou et al., "Vessicular glutamate transporters 1 and 2 are differentially associated with auditory nerve and spinal trigeminal inputs to the cochlear nucleus," The Journal of Comparative Neurology, Feb. 2007, 500(4):777-787.

\* cited by examiner

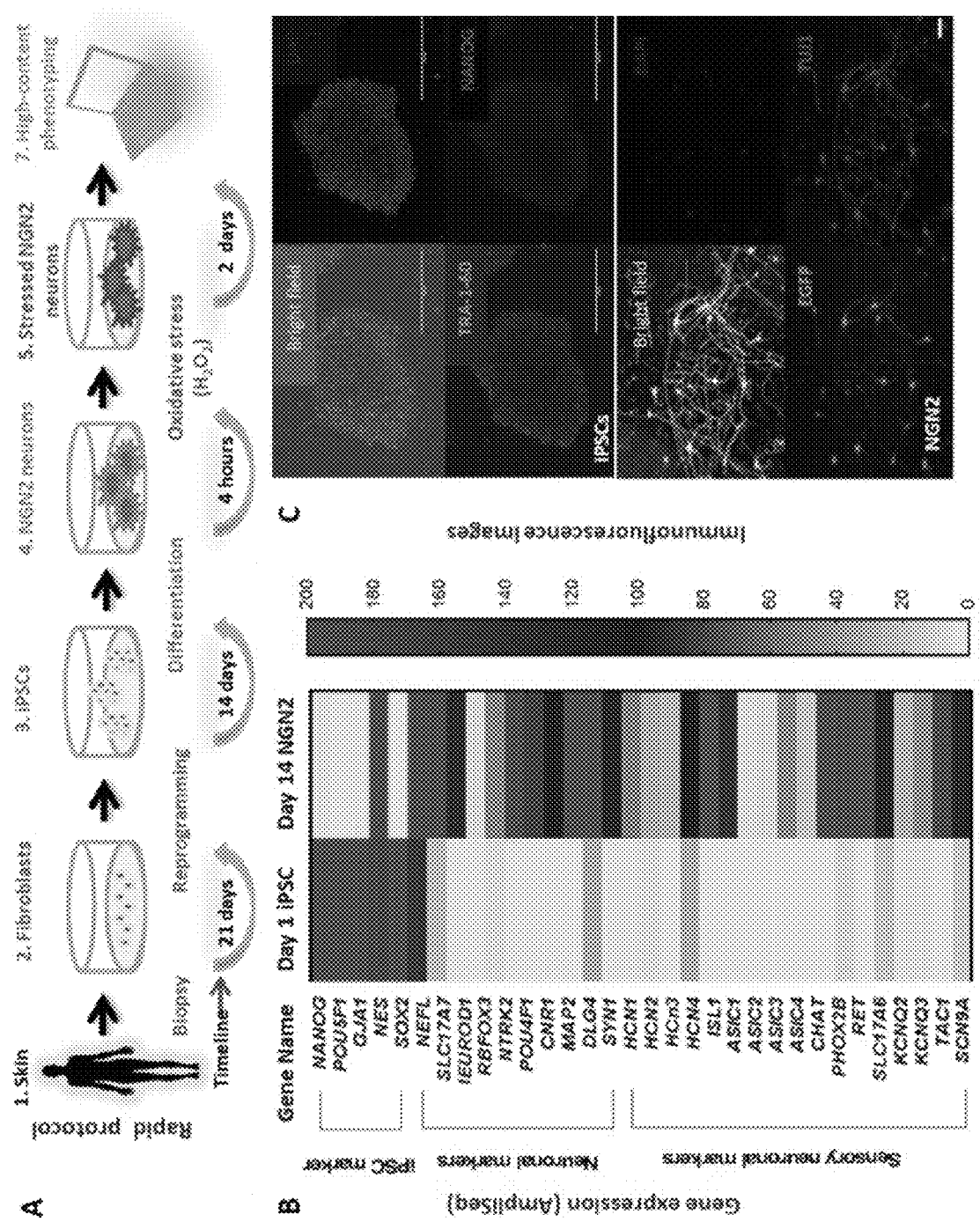
FIGs. 2A-C

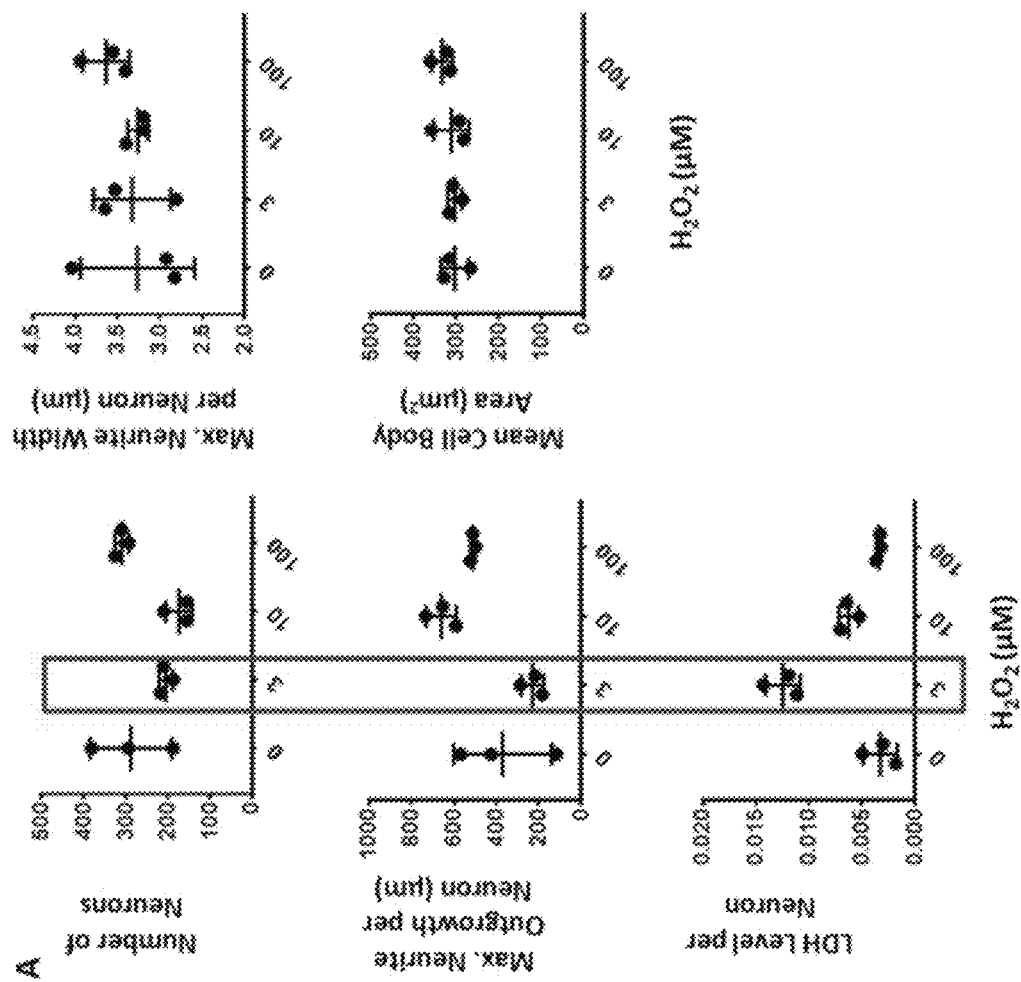
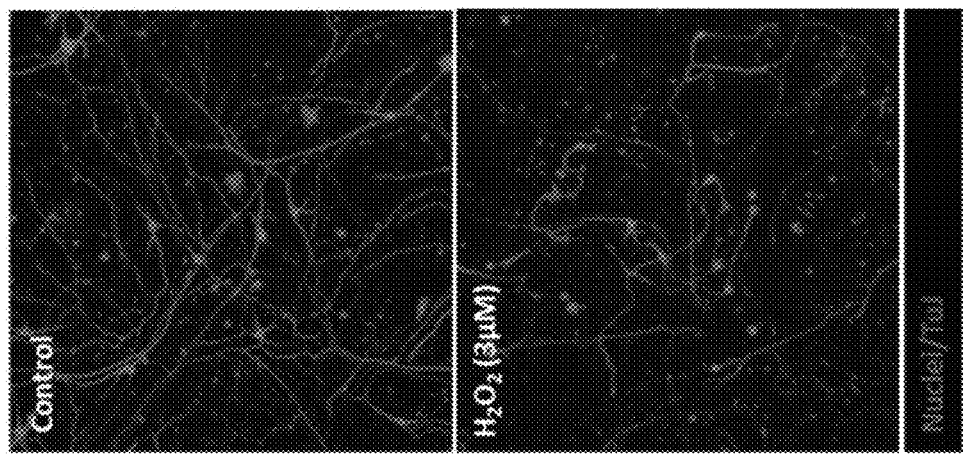
FIGs. 3A-B

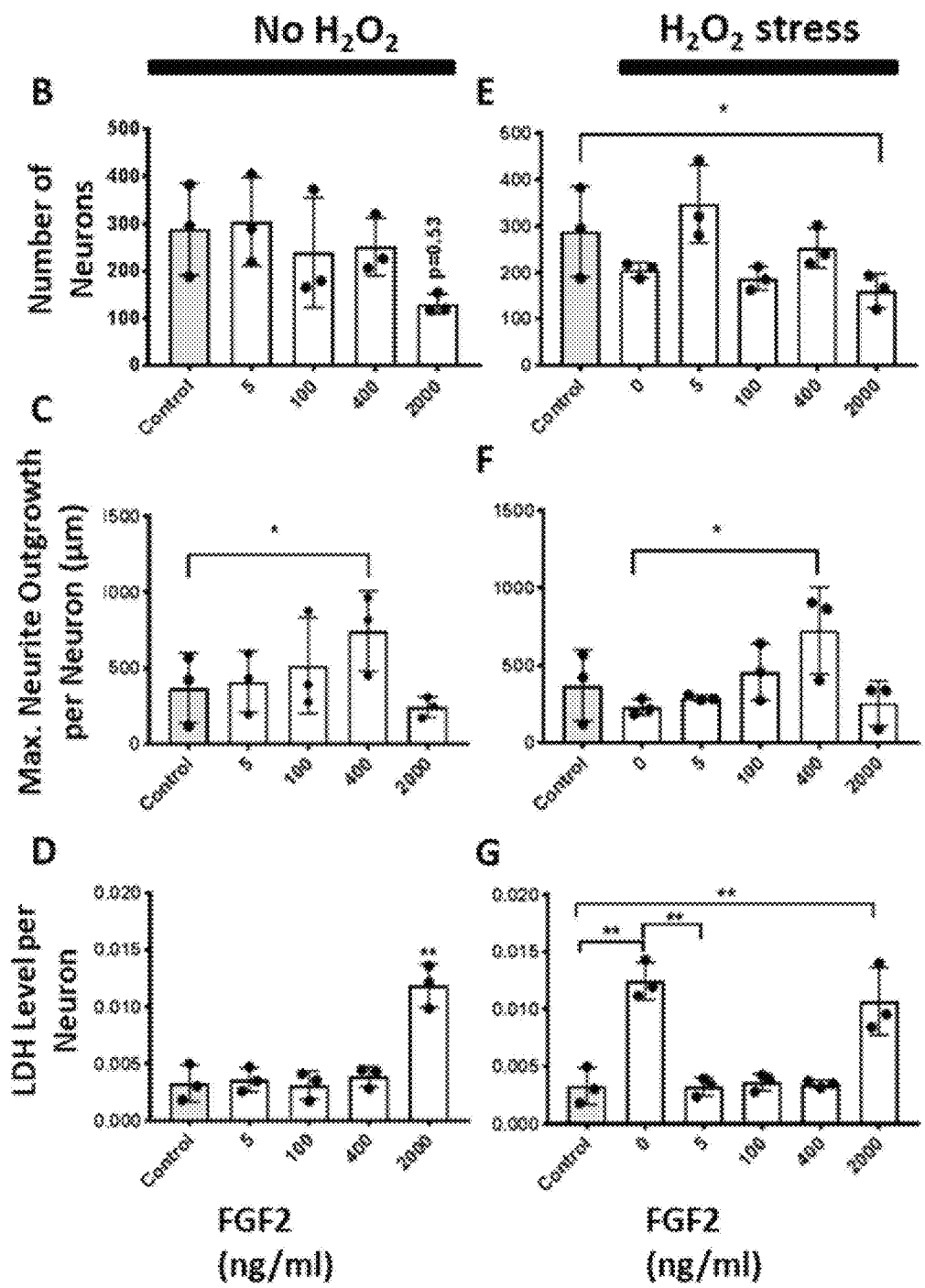
FIGs. 4B-G

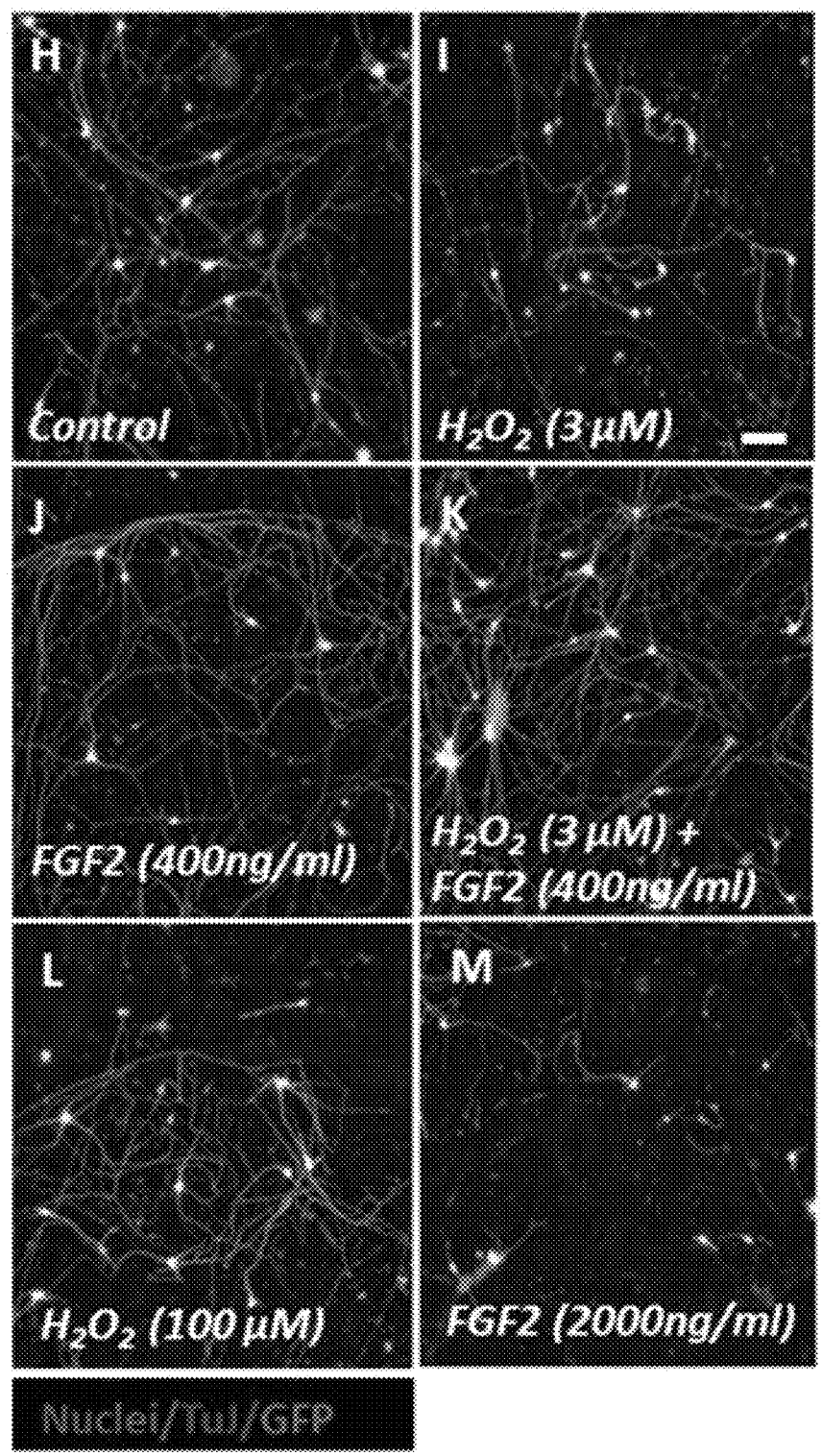
FIGs. 4H-M

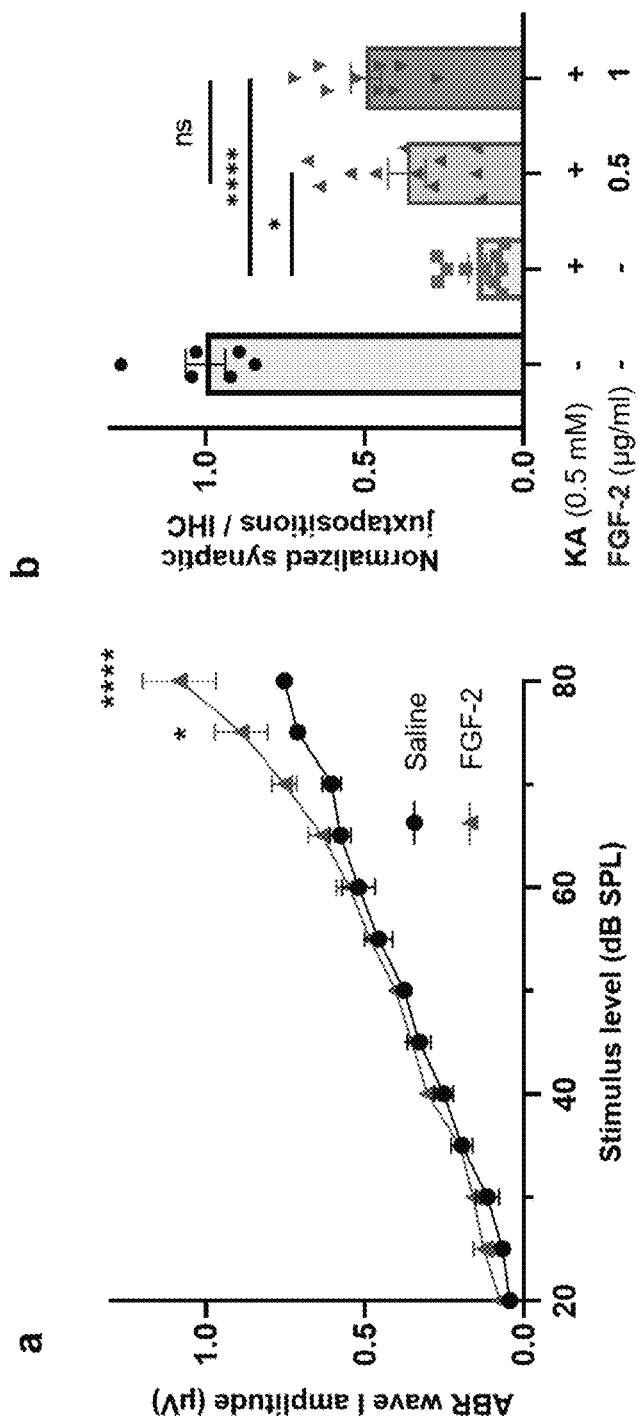
FIGS. 5A-B

METHODS OF TREATING SENSORINEURAL HEARING LOSS USING FIBROBLAST GROWTH FACTOR 2 (FGF2)

CLAIM OF PRIORITY

This application is a national stage entry of PCT/US2020/035198, filed on May 29, 2020, which claims the benefit of U.S. Provisional Patent Application Ser. No. 62/854,287, filed on May 29, 2019. The entire contents of the foregoing are hereby incorporated by reference.

FEDERALLY SPONSORED RESEARCH OR DEVELOPMENT

This invention was made with Government support under Grant No. DC015824 awarded by the National Institutes of Health. The Government has certain rights in the invention.

SEQUENCE LISTING

This application contains a Sequence Listing that has been submitted electronically as an ASCII text file named "00633-0264US1SequenceListing.txt". The ASCII text file, created on Nov. 23, 2021, is 1,717 bytes in size. The material in the ASCII text file is hereby incorporated by reference in its entirety.

TECHNICAL FIELD

Described herein are methods of using Fibroblast growth factor 2 (FGF2) to treat subjects with hearing loss associated with impaired word recognition.

BACKGROUND

Hearing loss is a worldwide problem of striking magnitude with no FDA-approved drugs. Disabling hearing loss affects 466 million people across the globe and that number is expected to increase to 900 million by 2050[1]. The annual cost of unaddressed hearing loss is $750 billion globally[1] and over $56 billion in the United States[2]. Most of this burden is due to sensorineural hearing loss (SNHL). Despite these astounding statistics, pharmacological therapies for SNHL are virtually nonexistent.

SUMMARY

The present disclosure addresses a major bottleneck in the auditory field: the need for robust, expandable, and biologically diverse cellular models that recapitulate the defining features of human disease and could be used to evaluate new biological therapies in a high throughput fashion. Described herein is the first human cellular model of acoustic trauma and synaptopathy. The experiments shown herein focused on inducing loss of neurites and synapses in that model because that pathology is known to underlie SNHL with compromised word recognition—the type of SNHL that is most socially disabling and for which current therapies (e.g., hearing aids and cochlear implants) have limited efficacy.

Thus, provided herein are methods for treating a subject who has sensorineural hearing loss (SNHL) with compromised word recognition. The methods include identifying a subject who has SNHL with compromised word recognition; and administering to the subject a therapeutically effective amount of Fibroblast growth factor 2 (FGF2) to the inner ear. Also provided is the use of FGF2 for treating a subject who has sensorineural hearing loss (SNHL) with compromised word recognition.

Also provided herein are methods for regenerating cochlear synapses in a subject. The methods include identifying a subject who has a loss of cochlear synapses; and administering to the subject a therapeutically effective amount of FGF2 to the inner ear. Also provided is the use of FGF2 for regenerating cochlear synapses in a subject who has a loss of cochlear synapses.

In some embodiments, the subject does not have tympanic membrane damage or rupture.

In some embodiments, the subject does not have tympanic membrane damage or rupture.

In some embodiments, the subject has sensorineural hearing loss (SNHL) with compromised word recognition, tinnitus or hyperacusis.

In some embodiments, the FGF2 is delivered via transtympanic delivery or intratympanic administration.

In some embodiments, the FGF2 is administered by implantation of a bioabsorbable matrix that releases FGF2 over time. In some embodiments, the bioabsorbable matrix comprises gelatin.

In some embodiments, the treatment results in an increase in wave I ABR, and the methods can optionally include measuring wave I ABR before and/or after treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A-C: Rapid generation, characterization and oxidative stressing of human induced pluripotent stem cell (iPSC)-derived NGN2 neurons. (A) Workflow diagram and timeline for rapid, single-step generation of NGN2 neurons from human skin-derived iPSCs. Differentiated NGN2 neurons express green fluorescent protein (green), and are subjected to $H_2O_2$ to induce oxidative stress (red). High-content phenotypic screening is performed using both IncuCyte (for live cell monitoring) and Array Scan (for quantification of neuronal morphology and immunostaining). (B) Heat map of changes in transcriptional profiles of NGN2 neurons after differentiation from iPSCs. All genes listed in this heat map as expressed by NGN2 neurons are also expressed in spiral ganglion neurons, except CHAT and PHOX2B. Mean expression levels from 3 different batches of NGN2 neurons are plotted. The cutoff value for saturating expression is set to 200 reads per million amplicons. The cutoff value for no expression is set to less than 10 reads per million amplicons. (C) Representative immunofluorescence images showing morphological and translational changes that characterize differentiation from iPSCs (expressing TRA-1-60 and NANOG) to NGN2 neurons (expressing EGFP and TUJI1). Scale bar 400 µm (iPSCs) and 50 µm (NGN2 neurons).

FIGS. 3A-B. Acoustic trauma model in human iPSC-derived NGN2 neurons. (A) NGN2 neurons were treated with different concentrations of $H_2O_2$ to simulate oxidative stress and resulting changes in neuronal number, maximal neurite outgrowth, mean cell body area, neurite width and LDH levels in culture media were quantified. 3 µm $H_2O_2$, tended to be most toxic (red rectangle). (B) NGN2 neuronal morphology before and after treatment with 3 µm $H_2O_2$. Neurofilament stained with TuJ antibody (red). Nuclei stained with DAPI (blue).

FIGS. 4A-M. FGF2 protects human iPSC-derived NGN2 neurons from $H_2O_2$-induced oxidative stress. (A) Workflow diagram and timeline for drug testing using stressed NGN2 neurons derived from human iPSCs. (B) Number of neurons, (C) maximal neurite outgrowth per neuron and (D) LDH release (absorbance at 490 nm) per neuron as a function of increasing FGF2 concentration in the absence of the $H_2O_2$ stressor or (E-G) following 3 µM $H_2O_2$ stress. Gray bars represent responses when control media was used (without $H_2O_2$ or FGF2). Each dot represents a separate experiment (N=3). Bars depict mean±SEM. *: p<0.05; **: p<0.01. (H-M): Representative images of NGN2 neurons after various experimental manipulations. (H) Control NGN2 neurons, not exposed to $H_2O_2$ or treated with FGF2. (I) Morphologic neuronal damage caused by exposure to 3 µM $H_2O_2$. (J) Neurite outgrowth stimulated by FGF2 at 400 ng/ml. (K) Neurons rescued from 3 µM $H_2O_2$-inflicted damage by post-treatment with FGF2 (400 ng/ml). (L) 100 µM $H_2O_2$ exposure is less toxic than 3 µM $H_2O_2$ exposure (H). (M) FGF2 at 2000 ng/ml is very toxic. NGN2 neurons express green GFP. Neurofilament is stained with TuJ antibody. DAPI labels nuclei.

FIGS. 5A-B. FGF-2 treatment rescues wave I ABR amplitude after neuropathic noise exposure in vivo and regenerates synapses at the IHC-SGN synapse in vitro. (A) Daily systemic FGF-2 administration for two weeks after exposure to 8-16 kHz noise at 97 dB SPL for 2 hours led to recovery of wave I ABR amplitude at 32 kHz—the frequency region of maximal neuropathic damage. Control, vehicle-treated animals demonstrated a statistically significant reduction in wave I ABR amplitude: 80 dB (**** P<0.0001) and 75 dB (* P=0.0329). N=4 ears for each group. (B) Cochlear explants were incubated with kainic acid (KA) for 2 h and treated with FGF-2 or media-only for 24 h. Quantification of CtBP2 and PSD95 juxtapositions per hair cell in cochlear explants normalized to media-only treatment. Data are presented as means±SEM. N=6-11 explants per group. * P=0.0107, **** P<0.0001. IHC, inner hair cell. SGN, spiral ganglion neuron.

DETAILED DESCRIPTION

Figure 1:
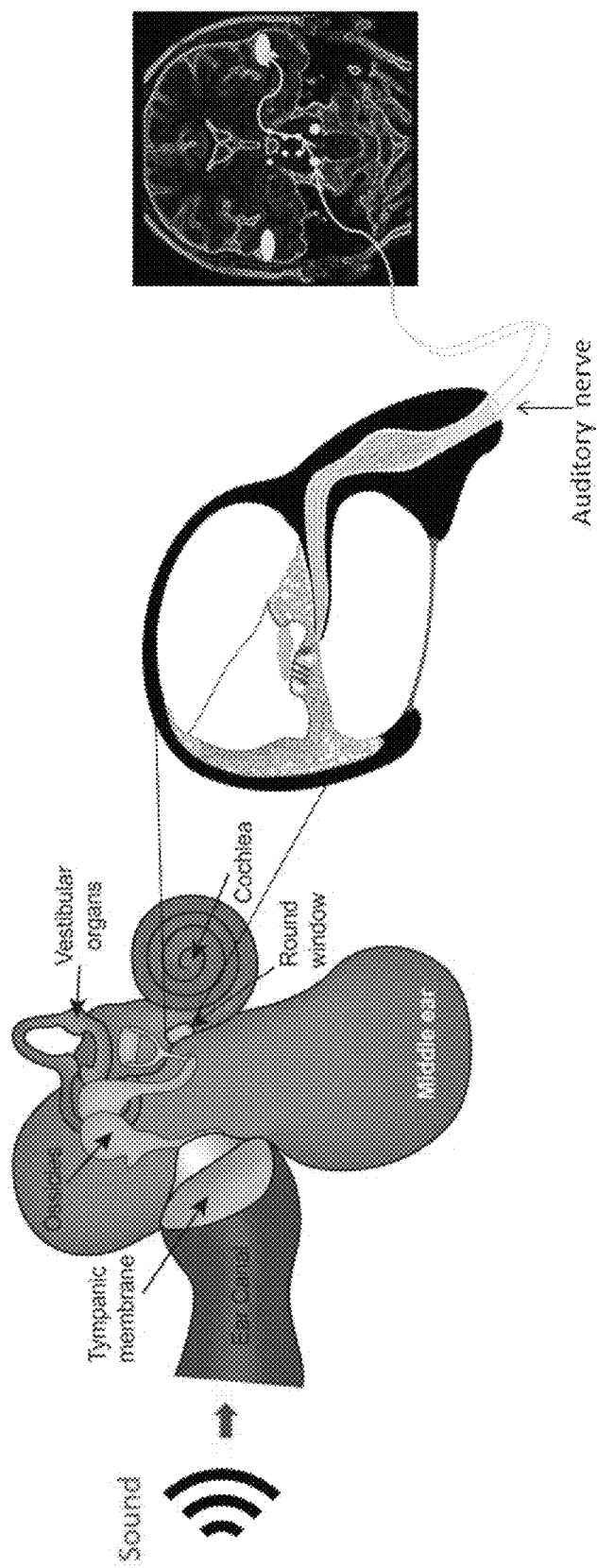
FIG. 1: Schematic of the hearing chain. A cochlear cross section depicts hair cells (blue), spiral ganglion neurons (yellow), and other cochlear cell types (gray). Brain scan on the right indicates auditory nuclei in the brain stem, midbrain and thalamus (yellow circles), as well as the primary auditory cortex (yellow ovals). Figure adapted in part from FIG. 1 of Mercier et al., Nat Biotechnol. 2012 December; 30(12): 1240-1243.
Figure 4A:
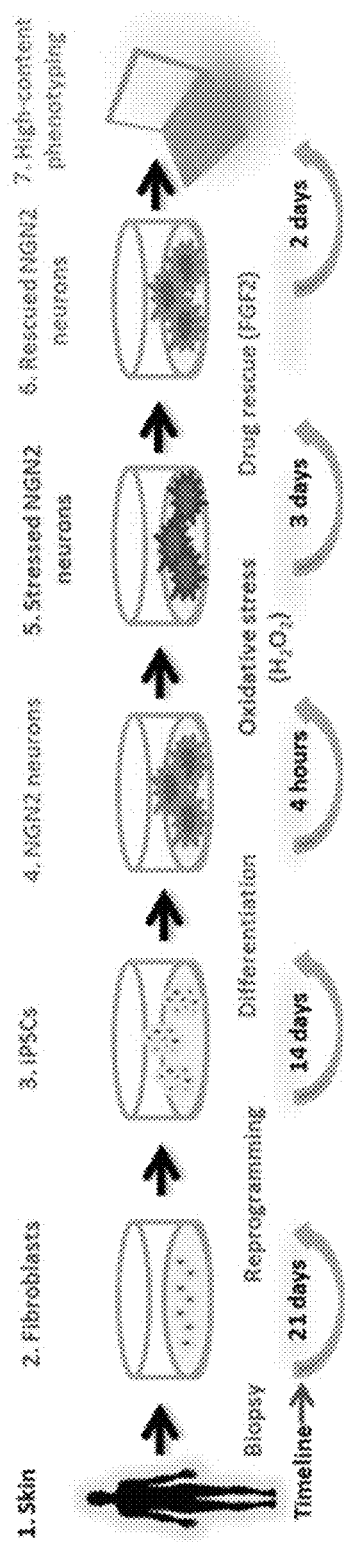

SNHL originates from defects in the cochlea, the tiny, snail-shaped organ that lies nestled within the densest bone in the human body (FIG. 1). Hearing begins when sound-induced vibrations of the tympanic membrane and middle ear bones are transmitted to cochlear fluids, leading to stimulation of sensory hair cells, neurotransmitter release, excitation of the auditory nerve, and transmission of the neural impulses through the auditory nuclei in the brainstem, midbrain, and thalamus to the auditory cortex (FIG. 1). There are approximately 30 different cell types in the cochlea and loss of or damage to any of these cell types can lead to hearing loss.

Common causes of human SNHL include exposure to loud noise and aging, which often damage sensory hair cells, resulting in elevated thresholds on the clinical audiogram. However, recent studies in animal models suggest that well before this overt hearing loss can be measured, a more insidious but likely more common process is taking place that permanently interrupts synaptic communication between sensory inner hair cells and subsets of cochlear nerve fibers[3-5]. Whether accompanied by audiometric threshold elevations or not, this "cochlear synaptopathy" alters auditory information processing and is a likely contributor to a variety of perceptual abnormalities, including compromised word recognition ability, difficulties understanding speech in noise, tinnitus, and hyperacusis[3]. It has long been recognized that word recognition testing is a much more sensitive metric of cochlear neural injury than audiometric thresholds, which can remain normal even when 80-90% of neurons are missing[6].

The identification of accessible, non-toxic drugs to treat cochlear synaptopathy and SNHL represents a major unmet medical need, as there are no FDA-approved pharmacotherapies for SNHL. Therapies for SNHL are essentially limited to hearing aids, which amplify sound, and cochlear implants, which electrically stimulate the cochlear nerve. However, the efficacy of these devices is variable among individuals and these devices do not restore word recognition to normal. Many new therapies are being developed that aim to restore function to damaged cells and nerves in the cochlea, including next-generation cochlear implants[7], gene therapy[8,9], and other small molecule and nanotherapies[10,11] Although numerous drugs and supplements have shown efficacy in animal models of SNHL, very few have translated to the clinic (as reviewed in [12] and [11]) Recent US clinical trials of compounds with disclosed mechanisms of action most commonly target cell death pathways and oxidative stress pathways known to be associated with SNHL[11]. None of these approaches specifically target the synaptic loss and neurite retraction that are the hallmarks of cochlear synaptopathy.

Identifying a drug that can promote regeneration of cochlear neurites and synapses would have transformative impact for people with hearing loss because loss of cochlear neurites is thought to be the main mechanism of reduced ability to understand speech, even when audiometric thresholds are not substantially affected. Compromised word understanding is particularly disabling because it continues to be an issue even for the most faithful users of hearing aids and cochlear implants. Consequently, SNHL is physically and emotionally costly to individuals, in addition to being economically costly to society[17]. Hearing loss has been linked to cognitive dysfunction[18], dementia[19], increased risk for depression in the elderly[20], and social and emotional loneliness[21].

FGF2

As shown herein, FGF2 (also known as basic FGF, bFGF) can promote synaptic and neurite regeneration in a human model of acoustic trauma. Cellular regeneration via FGF2 can be used to catalyze the restoration of acoustic hearing in people and improve their ability to understand words and speech in noise. The present methods can be used, e.g., in individuals struggling with presently irreversible SNHL and reduced word comprehension, which includes the vast majority of people with noise-induced and age-related SNHL.

FGF2 is a potent molecule with pleotropic biological effects that is already in clinical trials[57-83] and studies for a variety of diseases where it promotes wound healing, tissue regeneration and angiogenesis. Therefore, FGF2 is an attractive and safe candidate for repurposing in SNHL.

FGF2 has been extensively studied in animal models of hearing loss because FGF2 has known neurotrophic properties and plays important roles in the differentiation and function of the peripheral[22] and central nervous system[23]. Most animal studies of FGF2 have provided evidence that FGF2 can protect hair cells and cochlear neurons from aminoglycoside-mediated hair cell death[24], glutamate neurotoxicity[25] and mechanical damage[26] in vitro and from acoustic trauma in vivo[25,27,28]. However, other experiments have found no effect of FGF2 on dissociated murine cochlear neurons[29] in vitro or cochlear response to acoustic trauma in vivo[30]. These mixed results may be explained by small sample sizes and animal models that do not properly recapitulate human SNHL. Taken together, the present observations and the robust body of literature supporting a protective role of FGF2 in the mammalian auditory system strongly suggest that FGF2 can rescue degeneration of synapses and neurites in human neurons that model acoustic trauma.

The present results were unexpected because previous animal experiments had shown mixed results[24,25,26, 27, 28, 29, 30] and previously published reports by others explicitly attribute the observed improvements in word recognition after FGF2 application to the middle ear to promote tympanic membrane regeneration entirely to the closure of the tympanic membrane. See, e.g., Hakuba et al., The Laryngoscope 113, 1352-1355 (2003); Kanemaru et al., Otology & neurotology: official publication of the American Otological Society, American Neurotology Society [and] European Academy of Otology and Neurotology 32, 1218-1223 (2011); Omae et al., Auris Nasus Larynx 44, 664-671 (2017).

In some embodiments, the FGF2 is recombinant human FGF2 (rhFGF2). An exemplary sequence of human FGF2 is available in GenBank at Acc. No. NP_001997.5. In some embodiments, the FGF2 comprises Prol43-Ser288, e.g., as follows:

(SEQ ID NO: 1)
PALPEDGGSGAFPPGHFKDPKRLYCKNGGFFLRIHPDGRVDGVREKSDPH

IKLQLQAEERGVVSIKGVCANRYLAMKEDGRLLASKCVTDECFFFERLES

NNYNTYRSRKYTSWYVALKRTGQYKLGSKTGPGQKAILFLPMSAKS.

In some embodiments, the sequence includes an additional N-terminal Ala. rhFGF2 can be obtained commercially, e.g., from miltenyi biotech, R&D systems, Akron Biotech, Genscript, See also Aviles et al., Br J Pharmacol. 2003 October; 140(4): 637-646.

Methods of Treatment

The methods described herein include methods for the treatment of disorders associated with synaptic loss. In some embodiments, the disorder is sensorineural hearing loss with compromised word recognition. Generally, the methods include administering a therapeutically effective amount of FGF2 as described herein, to a subject who is in need of, or who has been determined to be in need of, such treatment.

As used in this context, to "treat" means to ameliorate at least one symptom of the disorder associated with synaptic loss. For example, a treatment can result in an increase in synaptic connections, or a decrease in the rate of loss of synapses.

As demonstrated herein, FGF2 can be used for SNHL with compromised word recognition, via localized, minimally invasive transtympanic delivery of FGF2 to the inner ear. Administration of a therapeutically effective amount of FGF2 for the treatment of sensorineural hearing loss with compromised word recognition will result in improved word recognition.

Because cochlear loss of synapses and neurites underlies tinnitus and hyperacusis, FGF2 can be used for treatment of tinnitus and hyperacusis, via localized transtympanic delivery of FGF2 to the inner ear. Administration of a therapeutically effective amount of FGF2 for the treatment of tinnitus will result in reduced tinnitus. Administration of a therapeutically effective amount of FGF2 for the treatment of hyperacusis will result in reduced sensitivity to sound.

FGF2 can also be used for treatment of synaptopathies in developmental or neurodegenerative diseases that affect other parts of the nervous system, including the brain and spinal cord. This could be accomplished via localized delivery of FGF2 to the brain, directly or via the inner ear. These synaptopathies may manifest as neurocognitive decline (such as memory loss and learning deficits) induced by therapies (including radiation, chemotherapy and surgery) for CNS neoplasms; these synaptopathies may manifest as psychiatric disorders (such as depression). Administration of a therapeutically effective amount of FGF2 for the treatment of these diseases will result in improvements in neurocognition and/or mood.

Thus the present methods can include administering an effective amount of FGF2 directly to an affected area, e.g., the inner ear or to the brain. The methods can include identifying a subject as being in need of such treatment. For example, a subject can be identified as having (or diagnosed with) SNHL with compromised word recognition, i.e. word recognition or speech discrimination of less than 80%, using an accepted diagnostic method, e.g., NU-6 by difficulty, CID W-22, Harvard-50. See, e.g., Halpin et al., Otol Neurotol, 33 (2012), pp. 907-911; Chen et al., Otol Neurotol, 24 (2003), pp. 728-733. In some embodiments, the subject does not have a ruptured or damaged cochlear membrane; otosclerosis; immune mediated SNHL; non-SNHL; ototoxicity; or congenital SNHL.

In some embodiments, the FGF2 is administered in a composition formulated using one or more physiologically acceptable carriers or excipients. In some embodiments, the FGF2 is the only active agent in the composition. In some embodiments, the pharmaceutical composition can be formulated for local or systemic administration, e.g., administration by drops (e.g., otic drops) or injection into the ear or other target tissue, or by implantation of a pump or other sustained release device or composition. The devices and pharmaceutical compositions can be administered directly and/or locally by injection or through surgical placement, e.g., via intratympanic or intracochlear administration, to the inner ear.

The composition can be, e.g., prepared with carriers that will protect the therapeutic compounds against rapid elimination from the body, such as a controlled release formulation, including implants and microencapsulated delivery systems. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811 and Mohammadian et al., Cell Mol Biol (Noisy-le-grand) 2017 January 30;63(1):28-33. Nanoparticles, e.g., poly lactic/glycolic acid (PLGA) nanoparticles (see Tamura et al., Laryngoscope. 2005 November; 115(11): 2000-5; Ge et al., Otolaryngol Head Neck Surg. 2007 October; 137(4):619-23; Horie et al., Laryngoscope. 2010 February; 120(2):377-83; Sakamoto et al., Acta Otolaryngol Suppl. 2010 November;(563):101-4) can also be used.

Bioabsorbable polymers and hydrogels for use in making matrices or sponges for use in the present methods are known in the art, see, e.g., Paulson et al., Laryngoscope. 2008 April; 118(4):706-11 (describing a chitosan-glycerophosphate (CGP)-hydrogel based drug delivery system), Igai et al., J Thorac Cardiovasc Surg. 2007 July; 134(1): 170-5 (describing a gelatin sponge; exemplary gelatin sponges are commercially available, e.g., Gelfoam, from Upjohn Company, Kalamazoo, MI; surgifoam, from ethicon), and Takemoto et al., Tissue Eng Part A. 2008 October; 14(10):1629-38 (describing gelatin and gelatin/collagen sponges); other carriers can include thermo-reversible tri-block copolymer poloxamer 407 (see, e.g., Wang et al., Audiol Neurootol. 2009; 14(6):393-401. Epub 2009 November 16, and Wang et al., Laryngoscope. 2011 February; 121(2):385-91); poloxamer-based hydrogels such as the one used in OTO-104 (see, e.g., GB2459910; Wang et al., Audiol Neurotol 2009; 14:393-401; and Piu et al., Otol Neurotol. 2011 January; 32(1):171-9); Pluronic F-127 (see, e.g., Escobar-Chavez et al., J Pharm Pharm Sci. 2006; 9(3):339-5); Pluronic F68, F88, or F108; polyoxyethylene-polyoxypropylene triblock copolymer (e.g., a polymer composed of polyoxypropylene and polyoxyethylene, of general formula E106 P70 E106; see GB2459910, US20110319377 and US20100273864); MPEG-PCL diblock copolymers (Hyun et al., Biomacromolecules. 2007 April; 8(4):1093-100. Epub 2007 February 28); hyaluronic acid hydrogels (Borden et al., Audiol Neurootol. 2011; 16(1):1-11); gelfoam cubes (see, e.g., Havenith et al., Hearing Research, February 2011; 272(1-2):168-177); and gelatin hydrogels (see, e.g., Inaoka et al., Acta Otolaryngol. 2009 April; 129(4):453-7); other biodegradable, biocompatible polymers can be used, such as ethylene vinyl acetate, polyanhydrides, polyglycolic acid, collagen, polyorthoesters, and polylactic acid. Tunable self-assembling hydrogels made from natural amino acids L and D can also be used, e.g., as described in Hauser et al e.g. Ac-LD6-COOH (L) e.g. Biotechnol Adv. 2012 May-June; 30(3):593-603. Such formulations can be prepared using standard techniques, or obtained commercially, e.g., from Alza Corporation and Nova Pharmaceuticals, Inc.

Implantable pumps are described, e.g., in Gehrke et al., Int J Pharm. 2016 Jul. 25; 509(1-2):85-94.

In addition to the formulations described above, the compositions can also be formulated as a depot preparation. Such long acting formulations can be administered by implantation (e.g., into the inner ear). Thus, for example, the compositions can be formulated with suitable polymeric or hydrophobic materials (for example as an emulsion in an acceptable oil) or ion exchange resins, or as sparingly soluble derivatives, for example, as a sparingly soluble salt, or mixed with chemical permeation enhancers.

For additional information on methods that can be used for drug delivery to the inner ear, see, e.g., Salt and Plontke, Audiol Neurootol. 2009 November; 14(6): 350-360; Kechai et al., Int J Pharm. 2015 Oct. 15; 494(1):83-101; Salt and Hirose, Hear Res. 2018 May; 362:25-37; Rivera et al., Curr Drug Deliv. 2012 May; 9(3):231-42; Musazzi et al., Drug Deliv Transl Res. 2018 April; 8(2):436-449; Liu et al., Drug Dev Ind Pharm. 2018 September; 44(9):1395-1408; Glueckert et al., Hear Res. 2018 October; 368:10-27; Nyberg et al., Sci Transl Med. 2019 Mar. 6; 11(482). pii: eaao0935.

In some embodiments, the method comprise administering 10-50, e.g., 15-25, e.g., 20 µg rhFGF2, e.g., about 0.1 to 0.5 mL, e.g., about 0.2 mL of 100 µg/mL of FGF2, in a polymer matrix, e.g., in a gelatin matrix/sponge.

EXAMPLES

The invention is further described in the following examples, which do not limit the scope of the invention described in the claims.

Example 1. Human In Vitro Model of SNHL

We have developed a novel human in vitro model of SNHL using induced pluripotent stem cell (iPSC)-derived glutaminergic neurons that can be used to evaluate promising therapeutics. The major advantage of an iPSC-based approach to human hearing loss modeling and drug testing is that iPSCs are renewable, genetically representative, and capable of generating the quantities of cells necessary to conduct a robust drug study. Using human iPSCs, the first human cellular model of acoustic trauma was developed (FIGS. 2A-C). We focus on generating and evaluating glutaminergic neurons because glutamate is the main afferent neurotransmitter in the cochlea, and a robust method exists by which iPSCs can be induced into glutaminergic neurons quickly, in a single step, with nearly 100% yield and purity, by forced expression of a single transcription factor, neurogenin (NGN2)[39]. Although these "NGN2 neurons" have characteristics of cortical glutaminergic neurons, they are nonetheless useful in modeling cochlear synaptopathy because these neurons express many genes that are also expressed by spiral ganglion neurons (SGN) (FIG. 2B). For example, TUBB3 gene encoding class III β-Tubulin has been immunohistochemically detected in human SGNs[40], and is routinely used by us (e.g. [41,42]) and others to label rodent SGNs. NTRK2 gene encoding Neurotrophic Receptor Tyrosine Kinase 2 (also known as TRK-B) is the receptor for brain-derived neurotrophic factor, and is known to be abundantly expressed in rodent SGNs (e.g. [43]) SLC17A7 (also known as VGLUT1) encodes vesicular glutamate transporter 1, which has been reported in rodent SGNs (e.g. [44]). Voltage gated potassium channels play key roles in hearing and subunits KCNQ2 and KCNQ3 have been detected in mouse and guinea pig SGNs[45]. In fact, all but two neuronal and sensory neuronal genes listed in FIG. 2B (genes CHAT and PHOX2B) are known to be expressed in SGNs.

Because NGN2 neurons are generated by transducing iPSCs with a lentiviral vector expressing Ngn2 along with a puromycin resistance gene (to allow selection for cells expressing Ngn2) and a lentiviral vector expressing enhanced green fluorescent protein (eGFP), successfully transduced NGN2 neurons express eGFP (FIG. 2C). This allows easy tracking of neurons in culture and quantification of their morphology.

To model synaptopathy due to acoustic trauma, we have induced oxidative stress causing nerve injury by $H_2O_2$. We chose this stressors because we[46] and others[47-49] have used animal models to demonstrate that $H_2O_2$ successfully mimics oxidative stress in neurons, and oxidative stress is a primary initial event in the degenerative cascade observed after noise exposure[50-52]. We show that $H_2O_2$ treatment of iPSC-derived NGN2 neurons tends to cause loss of neurites and synapses and induce cellular stress, as measured by lactate dehydrogenase (LDH) secretion into culture media. LDH is a robust marker of cell stress and death [53,54], and has been extensively used to evaluate neurotoxicity of various drugs[55,56].

For every experimental manipulation, untreated cells have served as controls. We have defined an $H_2O_2$ concentration that effectively tended to cause degeneration of synapses and neurites in our 2D model of acoustic trauma (FIGS. 3A-B). To avoid erroneous estimates of neurite or synaptic counts, we verified automated counts using manual counts.

We next studied FGF2's efficacy in promoting synaptic and neurite regeneration in NGN2 neurons following $H_2O_2$-induced stress (FIGS. 4A-M). For every experimental manipulation, untreated cells served as controls. Based on assessing a range of FGF2 concentrations applied to $H_2O_2$-stressed iPSC-derived NGN2 neurons, 400 ng/ml appears to be an effective therapeutic dose for FGF2 to promote neurite extension in human NGN2 neurons (FIGS. 4A-M). We have also identified a toxic concentration of FGF2 (2000 ng/ml), highlighting the need to carefully define the dose-response curve for FGF2.

When comparing responses from control and stressed or treated iPSC-derived NGN2 neurons, we have use t-tests (two-tailed, unpaired)/ANOVA for continuous data and rank tests for nonparametric data (e.g. intensity of immunostaining), with Benjamini-Hochberg correction for multiple hypothesis testing. The multiple comparison-adjusted p values<0.05 are considered statistically significant.

Example 2. FGF-2 Treatment Rescues Wave I ABR Amplitude after Neuropathic Noise Exposure In Vivo and Regenerates Synapses at the IHC-SGN Synapse In Vitro Methods The following materials and methods were used in this Example.

Animals and Experimental Design:

Male CBA/CaJ mice were purchased from Jackson Laboratories. Seven-weeks-old mice were exposed to a noise band known to destroy cochlear synapses and cause cochlear neuropathy. Mice were randomly assigned to a group receiving a subcutaneous (SC) injection of 0.5 μg FGF-2 (N=2 animals) or a control group receiving SC injection of vehicle (saline) (N=2 animals) daily for 14 days starting immediately after noise exposure. Fourteen days after noise exposure, cochlear function was assessed with ABRs and DPOAEs in each ear. All experimental procedures were approved by the Institutional Animal Care and Use Committee of Massachusetts Eye and Ear and conducted in accordance with the NIH Guide for the Care and Use of Laboratory Animals.

Noise Exposure:

Mice were exposed to octave-band noise (8-16 kHz) for 2 h at 97 dB sound pressure level (SPL) in a reverberant, acoustically-transparent wire box on a rotating platform. Animals were awake and unrestrained during noise exposure. The noise was created digitally using a fifth-order Butterworth filter, amplified through a power amplifier (Crown D75A), and delivered by a loudspeaker (JBL2446H) coupled to an exponential horn in the roof of the box. Exposure levels were measured in each cage with a 0.25-inch Brüel and Kjær condenser microphone.

Cochlear Function Testing:

ABRs and DPOAEs were recorded as detailed previously (Jensen et al., 2015; Suzuki et al., 2016). The mice were anesthetized with ketamine (100 mg/kg) and xylazine (10 mg/kg) administered intraperitoneally. A custom acoustic system was used consisting of two miniature earphones serving as sound sources (CDMG150 008-03A, CUI) and a microphone (FG-23329-PO7, Knowles) coupled to a probe tube to measure sound pressure near the eardrum. DPOAEs were measured as ear canal pressure in response to two tones presented into the ear canal (f1 and f2, with f2/f1=1.2) at half octave steps, from f2=5.66-45.25 kHz, and in 5 dB intensity increments from 15 to 80 dB SPL. ABR responses to 5 ms tone pips were measured between subdermal electrodes (positive behind the ipsilateral pinna, negative at the vertex, and ground at the tail), amplified 10,000 times and filtered (0.3-3.0 kHz). For each frequency and sound level, 512 responses were recorded and averaged using custom LabVIEW data-acquisition software run on a PXI chassis (National Instruments Corp., Austin, Texas). The ABR waveforms were stacked from lowest to highest SPL, and visually inspected to define threshold as the first level at which a repeatable wave I was detected. ABR data were acquired in 5 dB intensity increments. ABR wave I amplitude was measured peak-to-peak using the ABR Peak Analysis software (Eaton-Peabody Laboratories). Cochlear function testing and data quantification was performed by the researcher blinded to the treatment group.

In Vitro Model of Cochlear Synaptopathy:

Cochlear explant cultures were prepared as previously described by our laboratory (Landegger, Dilwali, & Stankovic, 2017). Briefly, postnatal day 4 CBA/CaJ wild-type mice (Jackson Laboratory, ME) were decapitated, the temporal bones extracted and the otic capsule dissected away from the cochleae in Hank's Balanced Salt Solution (Life Technologies, NY). The spiral ligament and stria vascularis were gently stripped away from base to apex. The middle part was carefully dissected into a more apical and more basal part, containing sensory hair cells and spiral ganglion neurons. The tectorial and Reissner's membrane were removed. Explants were left overnight to attach onto 10 mm glass coverslips coated with Cell-Tak (BD Biosciences, CA, #354241) in a 35 mm culture dish with 4 wells in culture medium consisting of 98% DMEM, 1% ampicillin, and 1% N2 supplement at 37° C. and 5% C02 levels in sterile conditions. After microscopically confirming attachment, explants were treated with 0.5 mM kainic acid (Abcam, MA; #ab120100) diluted in culture medium to induce glutamatergic excitotoxicity (Kempfle et al., 2018; Q. Wang & Green, 2011; Yamahara et al., 2019). After 2 h, medium was exchanged, and explants cultured in either culture medium or supplemented with recombinant mouse FGF-2/bFGF (R&D Systems; #3139-FB) at 0.5 or 1 μg/ml. After treatment, cochlear explants were rinsed in PBS, fixed with 4% paraformaldehyde (Electron Microscopy Sciences, PA) in PBS for 20 minutes, washed with PBS and blocked in a blocking buffer consisting of 5% Normal Horse Serum (NHS, Sigma-Aldrich, MO) with 1% Triton-X (Integra Chemical, WA) for ½ hour at room temperature. Following primary antibodies diluted in 1% normal horse serum with 0.3% TX were used for immunostaining and incubated with over-night at room temperature: rabbit anti-myosin 7A at 1:500 (Proteus Biosciences; #25-6790) to label hair cells; mouse (IgG1) anti-CtBP2 (C-terminal Binding Protein) at 1:1000 (#612044, BD Transduction Labs) to label presynaptic ribbons; mouse (IgG2a) anti-PSD95 (post-synaptic density 95) at 1:1000 (#75-028, Neuromab) to label post-synaptic neural synapse patches. After washing in PBS three times, explants were incubated in species-appropriate secondary antibodies at 1:500 dilution for 1½ hours: Alexa Fluor 647-conjugated goat anti-mouse (IgG2a) (#A21131, Life Technologies); Alexa Fluor 568-conjugated goat anti-mouse (IgG1) (#A21124, Life Technologies); Pacific blue-conjugated chicken anti-rabbit (#A21443, Life Technologies). After washing 3 times in PBS, coverslips were mounted on glass slides using Vectashield (Vector Laboratories, CA, #H-1000) and the edges sealed with clear nail polish (Electron Microscopy Sciences, PA). Specimens were imaged with a Leica SP8 confocal microscope. First at 20× for an overview of the specimen. Then, focusing separately on standardized areas to the explant's right and left, images were taken at 63× and with additional 2.4× digital zoom to visualize the entire organ of Corti and the inner hair cell—neurite synapse, respectively. Z-stacks were transferred to Amira imaging software (Visage Imaging, version 5.2.2). Connected components and iso-surface functions were used to create 3D renderings to count for synaptic juxtapositions as previously described(Suzuki et al., 2016). Quantification was performed by the researcher blinded to the treatment group.

Statistical Analysis:

Statistical analysis was performed using GraphPad Prism 8.2.1. Statistical significance in ABR wave I amplitude was determined using ordinary two-way ANOVA with subsequent Tukey's multiple comparisons test. For in vitro synaptic juxtapositions, Tukey's multiple comparison test was employed following one-way ANOVA. A probability value of $P<0.05$ was considered statistically significant. All data are presented as means±standard errors of the mean (SEMs).

Results

As shown in FIG. 5A, daily systemic FGF-2 administration for two weeks after exposure to 8-16 kHz noise at 97 dB SPL for 2 hours led to recovery of wave I ABR amplitude at 32 kHz—the frequency region of maximal neuropathic damage. Control, vehicle-treated animals demonstrated a statistically significant reduction in wave I ABR amplitude: 80 dB $P<0.0001$) and 75 dB ($P=0.0329$).

As shown in FIG. 5B, when cochlear explants were incubated with kainic acid for 2 h and treated with FGF-2 or media-only, the number of CtBP2 and PSD95 juxtapositions per hair cell in cochlear explants was significantly increased.

REFERENCES

1. World Health Organization, who.int/en/news-room/fact-sheets/detail/deafness-and-hearing-loss (2018).
2. Davila E P, C.-M. A., Muennig P, Lee D J, Fleming L E, Ferraro K F, LeBlanc W G, Lam B L, Arheart K L, McCollister K E, Zheng D, Christ S L. Sensory impairment among older US workers. Am J Public Health, 1378-1385 (2009).
3. Liberman, M. C. & Kujawa, S. G. Cochlear synaptopathy in acquired sensorineural hearing loss: Manifestations and mechanisms. Hear Res 349, 138-147, doi:10.1016/j.heares.2017.01.003 (2017).
4. Liberman, M. C., Epstein, M. J., Cleveland, S. S., Wang, H. & Maison, S. F. Toward a Differential Diagnosis of Hidden Hearing Loss in Humans. PloS one 11, e0162726, doi:10.1371/journal.pone.0162726 (2016).
5. Furman, A. C., Kujawa, S. G. & Liberman, M. C. Noise-induced cochlear neuropathy is selective for fibers with low spontaneous rates. J Neurophysiol 110, 577-586, doi:10.1152/jn.00164.2013 (2013).
6. Schuknecht, H. F. & Woellner, R. C. An experimental and clinical study of deafness from lesions of the cochlear nerve. J Laryngol Otol 69, 75-97 (1955).
7. Senn, P. et al. NANOCI-Nanotechnology Based Cochlear Implant With Gapless Interface to Auditory Neurons. Otology & neurotology: official publication of the American Otological Society, American Neurotology Society [and] European Academy of Otology and Neurotology 38, e224-e231, doi:10.1097/MAO.0000000000001439 (2017).
8. Safety, Tolerability and Efficacy for CGF166 in Patients With Unilateral or Bilateral Severe-to-profound Hearing Loss.
9. Landegger, L. D. et al. A synthetic AAV vector enables safe and efficient gene transfer to the mammalian inner ear. Nat Biotechnol 35, 280-284, doi:10.1038/nbt.3781 (2017).
10. Kuroda, Y. et al. A pilot study of regenerative therapy using controlled release of recombinant human fibroblast growth factor for patients with pre-collapse osteonecrosis of the femoral head. International orthopaedics 40, 1747-1754, doi:10.1007/s00264-015-3083-1 (2016).
11. Crowson, M. G., Hertzano, R. & Tucci, D. L. Emerging Therapies for Sensorineural Hearing Loss. Otology & neurotology: official publication of the American Otological Society, American Neurotology Society [and] European Academy of Otology and Neurotology 38, 792-803, doi:10.1097/MAO.0000000000001427 (2017).
12. Muurling, T. & Stankovic, K. M. Metabolomic and network analysis of pharmacotherapies for sensorineural hearing loss. Otology & neurotology: official publication of the American Otological Society, American Neurotology Society [and] European Academy of Otology and Neurotology 35, 1-6, doi:10.1097/MAO.0000000000000254 (2014).
13. Fibroblast Growth Factor Regeneration of Tympanic Membrane Perforations. clinicaltrials.gov/ct2/show/NCT02307916?term=welling&rank=1
14. Hakuba, N. et al. A new method for closing tympanic membrane perforations using basic fibroblast growth factor. The Laryngoscope 113, 1352-1355, doi:10.1097/00005537-200308000-00016 (2003).
15. Kanemaru, S. et al. Regenerative treatment for tympanic membrane perforation. Otology & neurotology: official publication of the American Otological Society, American Neurotology Society [and] European Academy of Otology and Neurotology 32, 1218-1223, doi:10.1097/MAO.0b013e31822e0e53 (2011).
16. Omae, K. et al. Regenerative treatment for tympanic membrane perforation using gelatin sponge with basic fibroblast growth factor. Auris Nasus Larynx 44, 664-671, doi:10.1016/j.anl.2016.12.005 (2017).
17. West, J. S., Low, J. C. & Stankovic, K. M. Revealing Hearing Loss: A Survey of How People Verbally Disclose Their Hearing Loss. Ear and hearing 37, 194-205, doi:10.1097/AUD.0000000000000238 (2016).
18. Lin, F. R. et al. Hearing loss and cognition in the Baltimore Longitudinal Study of Aging. Neuropsychology 25, 763-770, doi:10.1037/a0024238 (2011).
19. Lin, F. R. et al. Hearing loss and incident dementia. Archives of neurology 68, 214-220, doi:10.1001/archneurol.2010.362 (2011).
20. Huang, C. Q., Dong, B. R., Lu, Z. C., Yue, J. R. & Liu, Q. X. Chronic diseases and risk for depression in old age:

21. Pronk, M. et al. Prospective effects of hearing status on loneliness and depression in older persons: identification of subgroups. International journal of audiology 50, 887-896, doi:10.3109/14992027.2011.599871 (2011).
22. Grothe, C., Haastert, K. & Jungnickel, J. Physiological function and putative therapeutic impact of the FGF-2 system in peripheral nerve regeneration—lessons from in vivo studies in mice and rats. Brain Res Rev 51, 293-299, doi:10.1016/j.brainresrev.2005.12.001 (2006).
23. Woodbury, M. E. & Ikezu, T. Fibroblast growth factor-2 signaling in neurogenesis and neurodegeneration. J Neuroimmune Pharmacol 9, 92-101, doi:10.1007/s11481-013-9501-5 (2014).
24. Low, W., Dazert, S., Baird, A. & Ryan, A. F. Basic fibroblast growth factor (FGF-2) protects rat cochlear hair cells in organotypical culture from aminoglycoside injury. J Cell Physiol 167, 443-450, doi:10.1002/(SICI)1097-4652(199606)167:3<443::AID-JCP8>3.0.CO;2-P (1996).
25. Zhai, S. Q., Wang, D. J., Wang, J. L., Han, D. Y. & Yang, W. Y. Basic fibroblast growth factor protects auditory neurons and hair cells from glutamate neurotoxicity and noise exposure. Acta Otolaryngol 124, 124-129 (2004).
26. Wei, D., Jin, Z., Jarlebark, L., Scarfone, E. & Ulfendahl, M. Survival, synaptogenesis, and regeneration of adult mouse spiral ganglion neurons in vitro. Dev Neurobiol 67, 108-122, doi:10.1002/dneu.20336 (2007).
27. Zhai, S. Q. et al. Protective effect of basic fibroblast growth factor on auditory hair cells after noise exposure. Acta Otolaryngol 122, 370-373 (2002).
28. Shi, L. et al. [Construction of bicistronic eukaryotic vector containing basic fibroblast growth factor and study of their functions in gene therapy for hearing impairment]. Zhonghua er bi yan hou ke za zhi 38, 21-23 (2003).
29. Rak, K. et al. Effects of the neurotrophic factors BDNF, NT-3, and FGF2 on dissociated neurons of the cochlear nucleus. Neuroreport 25, 960-964, doi:10.1097/WNR.0000000000000220 (2014).
30. Yamasoba, T. et al. Absence of hair cell protection by exogenous FGF-1 and FGF-2 delivered to guinea pig cochlea in vivo. Noise Health 3, 65-78 (2001).
31. Ebert, A. D. et al. Induced pluripotent stem cells from a spinal muscular atrophy patient. Nature 457, 277-280, doi:10.1038/nature07677 (2009).
32. Wainger, B. J. et al. Intrinsic membrane hyperexcitability of amyotrophic lateral sclerosis patient-derived motor neurons. Cell Rep 7, 1-11, doi:10.1016/j.celrep.2014.03.019 (2014).
33. Silva, M. C. et al. Human iPSC-Derived Neuronal Model of Tau-A152T Frontotemporal Dementia Reveals Tau-Mediated Mechanisms of Neuronal Vulnerability. Stem Cell Reports 7, 325-340, doi:10.1016/j.stemcr.2016.08.001 (2016).
0 34. Pasca, S. P. et al. Using iPSC-derived neurons to uncover cellular phenotypes associated with Timothy syndrome. Nature medicine 17, 1657-1662, doi:10.1038/nm.2576 (2011).
35. Shcheglovitov, A. et al. SHANK3 and IGF1 restore synaptic deficits in neurons from 22q13 deletion syndrome patients. Nature 503, 267-271, doi:10.1038/nature12618 (2013).
36. Sundberg, M. et al. Purkinje cells derived from TSC patients display hypoexcitability and synaptic deficits associated with reduced FMRP levels and reversed by rapamycin. Mol Psychiatry, doi:10.1038/s41380-018-0018-4 (2018).
37. Ohuchi, K. et al. Established Stem Cell Model of Spinal Muscular Atrophy Is Applicable in the Evaluation of the Efficacy of Thyrotropin-Releasing Hormone Analog. Stem Cells Transl Med 5, 152-163, doi:10.5966/sctm.2015-0059 (2016).
38. McNeish, J., Gardner, J. P., Wainger, B. J., Woolf, C. J. & Eggan, K. From Dish to Bedside: Lessons Learned While Translating Findings from a Stem Cell Model of Disease to a Clinical Trial. Cell stem cell 17, 8-10, doi:10.1016/j.stem.2015.06.013 (2015).
39. Zhang, Y. et al. Rapid single-step induction of functional neurons from human pluripotent stem cells. Neuron 78, 785-798, doi:10.1016/j.neuron.2013.05.029 (2013).
40. Locher, H. et al. Neurosensory development and cell fate determination in the human cochlea. Neural development 8, 20, doi:10.1186/1749-8104-8-20 (2013).
41. Kao, S. Y., Soares, V. Y., Kristiansen, A. G. & Stankovic, K. M. Activation of TRAIL-DR5 pathway promotes sensorineural degeneration in the inner ear. Aging cell 15, 301-308, doi:10.1111/acel.12437 (2016).
42. Dilwali, S., Landegger, L. D., Soares, V. Y., Deschler, D. G. & Stankovic, K. M. Secreted Factors from Human Vestibular Schwannomas Can Cause Cochlear Damage. Scientific reports 5, 18599, doi:10.1038/srep18599 (2015).
43. Farinas, I. et al. Spatial shaping of cochlear innervation by temporally regulated neurotrophin expression. The Journal of neuroscience: the official journal of the Society for Neuroscience 21, 6170-6180 (2001).
44. Zhou, J., Nannapaneni, N. & Shore, S. Vessicular glutamate transporters 1 and 2 are differentially associated with auditory nerve and spinal trigeminal inputs to the cochlear nucleus. The Journal of comparative neurology 500, 777-787, doi:10.1002/cne.21208 (2007).
45. Jin, Z., Liang, G. H., Cooper, E. C. & Jarlebark, L. Expression and localization of K channels KCNQ2 and KCNQ3 in the mammalian cochlea. Audiology & neurootology 14, 98-105, doi: 10.1159/000158538 (2009).
46. Kao, S. Y. et al. Loss of osteoprotegerin expression in the inner ear causes degeneration of the cochlear nerve and sensorineural hearing loss. Neurobiol Dis 56, 25-33, doi:10.1016/j.nbd.2013.04.008 (2013).
47. Kempfle, J. S. et al. Bisphosphonate-Linked TrkB Agonist: Cochlea-Targeted Delivery of a Neurotrophic Agent as a Strategy for the Treatment of Hearing Loss. Bioconjug Chem 29, 1240-1250, doi:10.1021/acs.bioconjchem.8b00022 (2018).
48. Wang, Q., Yu, S., Simonyi, A., Sun, G. Y. & Sun, A. Y. Kainic acid-mediated excitotoxicity as a model for neurodegeneration. Mol Neurobiol 31, 3-16, doi:10.1385/MN:31:1-3:003 (2005).
49. Hachem, L. D., Mothe, A. J. & Tator, C. H. Glutamate Increases In Vitro Survival and Proliferation and Attenuates Oxidative Stress-Induced Cell Death in Adult Spinal Cord-Derived Neural Stem/Progenitor Cells via Non-NMDA Ionotropic Glutamate Receptors. Stem Cells Dev 25, 1223-1233, doi:10.1089/scd.2015.0389 (2016).
50. Ruel, J. et al. Physiology, pharmacology and plasticity at the inner hair cell synaptic complex. Hear Res 227, 19-27, doi:10.1016/j.heares.2006.08.017 (2007).
51. Ruel, J. et al. Neuroprotective effect of riluzole in acute noise-induced hearing loss. Neuroreport 16, 1087-1090 (2005).

52. Kujawa, S. G. & Liberman, M. C. Adding insult to injury: cochlear nerve degeneration after "temporary" noise-induced hearing loss. The Journal of neuroscience: the official journal of the Society for Neuroscience 29, 14077-14085, doi:10.1523/JNEUROSCI.2845-09.2009 (2009).

53. Kendig, D. M. & Tarloff, J. B. Inactivation of lactate dehydrogenase by several chemicals: implications for in vitro toxicology studies. Toxicology in vitro: an international journal published in association with BIBRA 21, 125-132, doi:10.1016/j.tiv.2006.08.004 (2007).

54. Lee, S. J. et al. Ciclopirox protects mitochondria from hydrogen peroxide toxicity. British journal of pharmacology 145, 469-476, doi:10.1038/sj.bjp.0706206 (2005).

55. Smith, S. M., Wunder, M. B., Norris, D. A. & Shellman, Y. G. A simple protocol for using a LDH-based cytotoxicity assay to assess the effects of death and growth inhibition at the same time. PloS one 6, e26908, doi: 10.1371/journal.pone.0026908 (2011).

56. Chan, F. K., Moriwaki, K. & De Rosa, M. J. Detection of necrosis by release of lactate dehydrogenase activity. Methods in molecular biology 979, 65-70, doi:10.1007/978-1-62703-290-2_7 (2013).

57. Hakuba, N. et al. A new method for closing tympanic membrane perforations using basic fibroblast growth factor. The Laryngoscope 113, 1352-1355, doi:10.1097/00005537-200308000-00016 (2003).

58. Hakuba, N. et al. Basic fibroblast growth factor combined with atelocollagen for closing chronic tympanic membrane perforations in 87 patients. Otology & neurotology: official publication of the American Otological Society, American Neurotology Society [and] European Academy of Otology and Neurotology 31, 118-121, doi: 10.1097/MAO.0b013e3181c34f01 (2010).

59. Lou, Z., Tang, Y. & Wu, X. Analysis of the effectiveness of basic fibroblast growth factor treatment on traumatic perforation of the tympanic membrane at different time points. American journal of otolaryngology 33, 244-249, doi:10.1016/j.amjoto.2011.07.006 (2012).

60. Acharya, A. N., Coates, H., Tavora-Vieira, D. & Rajan, G. P. A pilot study investigating basic fibroblast growth factor for the repair of chronic tympanic membrane perforations in pediatric patients. International journal of pediatric otorhinolaryngology 79, 332-335, doi:10.1016/j.ijporl.2014.12.014 (2015).

61. Kakigi, A., Sawada, S. & Takeda, T. The effects of basic fibroblast growth factor on postoperative mastoid cavity problems. Otology & neurotology: official publication of the American Otological Society, American Neurotology Society [and] European Academy of Otology and Neurotology 26, 333-336; discussion 336 (2005).

62. Huang, Y. F., Wang, L. Q., Du, G. P., Zhang, Y. H. & Ge, M. [The effect of recombinant bovine basic fibroblast growth factor on the LASIK-induced neurotrophic epitheliopathy and the recovery of corneal sensation after LASIK]. [Zhonghua yan ke za zhi] Chinese journal of ophthalmology 47, 22-26 (2011).

63. Meduri, A. et al. Effect of the combination of basic fibroblast growth factor and cysteine on corneal epithelial healing after photorefractive keratectomy in patients affected by myopia. Indian journal of ophthalmology 62, 424-428, doi:10.4103/0301-4738.119420 (2014).

64. Kitamura, M. et al. Periodontal tissue regeneration using fibroblast growth factor-2: randomized controlled phase II clinical trial. PloS one 3, e2611, doi:10.1371/journal.pone.0002611 (2008).

65. de Santana, R. B. & de Santana, C. M. Human intrabony defect regeneration with rhFGF-2 and hyaluronic acid—a randomized controlled clinical trial. Journal of clinical periodontology 42, 658-665, doi:10.1111/jcpe.12406 (2015).

66. Cochran, D. L. et al. A Randomized Clinical Trial Evaluating rh-FGF-2/beta-TCP in Periodontal Defects. Journal of dental research 95, 523-530, doi:10.1177/0022034516632497 (2016).

67. Hull, M. A. et al. Healing with basic fibroblast growth factor is associated with reduced indomethacin induced relapse in a human model of gastric ulceration. Gut 40, 204-210 (1997).

68. Akita, S. et al. Basic fibroblast growth factor is beneficial for postoperative color uniformity in split-thickness skin grafting. Wound repair and regeneration: official publication of the Wound Healing Society [and] the European Tissue Repair Society 18, 560-566, doi:10.1111/j.1524-475X.2010.00620.x (2010).

69. Kawaguchi, H. et al. Local application of recombinant human fibroblast growth factor-2 on bone repair: a dose-escalation prospective trial on patients with osteotomy. Journal of orthopaedic research: official publication of the Orthopaedic Research Society 25, 480-487, doi:10.1002/jor.20315 (2007).

70. Fu, X. et al. Randomised placebo-controlled trial of use of topical recombinant bovine basic fibroblast growth factor for second-degree burns. Lancet 352, 1661-1664, doi:10.1016/S0140-6736(98)01260-4 (1998).

71. Akita, S., Akino, K., Imaizumi, T. & Hirano, A. Basic fibroblast growth factor accelerates and improves second-degree burn wound healing. Wound repair and regeneration: official publication of the Wound Healing Society [and] the European Tissue Repair Society 16, 635-641, doi:10.1111/j.1524-475X.2008.00414.x (2008).

72. Han, Y. & Liu, J. [Autologous free fat particle grafting combined with bFGF to repair facial depression]. Zhongguo xiu fu chong jian wai ke za zhi=Zhongguo xiufu chongjian waike zazhi=Chinese journal of reparative and reconstructive surgery 22, 339-342 (2008).

73. Mu, J., Zhang, X., Cheng, J. & Yuan, Y. [Effects of bFGF on the nasal mucosa after endoscopic sinus surgery]. Lin chuang er bi yan hou ke za zhi=Journal of clinical otorhinolaryngology 19, 646-647 (2005).

74. Liu, H., Gao, Z., Song, Y. & Lu, M. [Absorbable shanching satin rb-bFGF prepreg sheet and expansion hemostatic sponge together to cure epistaxis with blood disease]. Lin chuang er bi yan hou tou jing wai ke za zhi=Journal of clinical otorhinolaryngology, head, and neck surgery 28, 126-128 (2014).

75. Liu, B., Jiang, Y. H., Xiao, J. & Li, X. K. [Efficacy of bFGF atomization inhalation on postoperative sore throat following oral and maxillofacial surgery under general anesthesia]. Shanghai kou qiang yi xue=Shanghai journal of stomatology 25, 497-499 (2016).

76. Hirano, S., Kishimoto, Y., Suehiro, A., Kanemaru, S. & Ito, J. Regeneration of aged vocal fold: first human case treated with fibroblast growth factor. The Laryngoscope 118, 2254-2259, doi:10.1097/MLG.0b013e3181845720 (2008).

77. Kusuhara, H., Itani, Y., Isogai, N. & Tabata, Y. Randomized controlled trial of the application of topical b-FGF-impregnated gelatin microspheres to improve tissue survival in subzone II fingertip amputations. The Journal of hand surgery, European volume 36, 455-460, doi: 10.1177/1753193411402761 (2011).

78. Sellke, F. W., Laham, R. J., Edelman, E. R., Pearlman, J. D. & Simons, M. Therapeutic angiogenesis with basic fibroblast growth factor: technique and early results. The Annals of thoracic surgery 65, 1540-1544 (1998).
79. Morimoto, N. et al. Novel collagen/gelatin scaffold with sustained release of basic fibroblast growth factor: clinical trial for chronic skin ulcers. Tissue engineering. Part A 19, 1931-1940, doi:10.1089/ten.TEA.2012.0634 (2013).
80. Robson, M. C. et al. The safety and effect of topically applied recombinant basic fibroblast growth factor on the healing of chronic pressure sores. Annals of surgery 216, 401-406; discussion 406-408 (1992).
81. Marui, A. et al. A novel approach to therapeutic angiogenesis for patients with critical limb ischemia by sustained release of basic fibroblast growth factor using biodegradable gelatin hydrogel: an initial report of the phase I-IIa study. Circulation journal: official journal of the Japanese Circulation Society 71, 1181-1186 (2007).
82. Yonemitsu, Y. et al. DVC1-0101 to treat peripheral arterial disease: a Phase I/IIa open-label dose-escalation clinical trial. Molecular therapy: the journal of the American Society of Gene Therapy 21, 707-714, doi:10.1038/mt.2012.279 (2013).
83. Lederman, R. J. et al. Therapeutic angiogenesis with recombinant fibroblast growth factor-2 for intermittent claudication (the TRAFFIC study): a randomised trial. Lancet 359, 2053-2058 (2002).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has cochlear synaptopathy and does not have tympanic membrane damage or rupture, the method comprising:
   identifying a subject who has cochlear synaptopathy but who does not have tympanic membrane damage or rupture; and
   administering to the subject a therapeutically effective amount of Fibroblast growth factor 2 (FGF2) to the inner ear,
   wherein the therapeutically effective amount of FGF2 is an amount sufficient to improve word recognition in the subject.

2. The method of claim 1, wherein the FGF2 is delivered via transtympanic delivery.

3. The method of claim 1, wherein the FGF2 is administered by intratympanic administration.

4. The method of claim 3, wherein the FGF2 is administered by implantation of a bioabsorbable matrix that releases FGF2 over time.

5. The method of claim 4, wherein the bioabsorbable matrix comprises gelatin.

6. The method of claim 1, wherein the method further comprises measuring wave I ABR before and after treatment.

7. A method of regenerating cochlear synapses in a subject, the method comprising:
   identifying a subject who has a loss of cochlear synapses, but who does not have tympanic membrane damage or rupture; and
   administering to the subject a therapeutically effective amount of FGF2 to the inner ear.

8. The method of claim 7, wherein the FGF2 is delivered via transtympanic delivery.

9. The method of claim 8, wherein the FGF2 is an amount sufficient to improve word recognition in the subject.

* * * * *

SEQUENCE LISTING

```
<160> NUMBER OF SEQ ID NOS: 1

<210> SEQ ID NO 1
<211> LENGTH: 146
<212> TYPE: PRT
<213> ORGANISM: Artificial
<220> FEATURE:
<223> OTHER INFORMATION: Pro143-Ser288 of human FGF2

<400> SEQUENCE: 1

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145
```